US012780903B2

(12) United States Patent
Neumeier et al.

(10) Patent No.: US 12,780,903 B2
(45) Date of Patent: Nov. 3, 2026

(54) METHOD TO PRODUCE AN IMMUNOGLOBULIN PREPARATION FROM C-1 INHIBITOR DEPLETED PLASMA

(71) Applicant: Takeda Pharmaceutical Company Limited, Osaka (JP)

(72) Inventors: Ursula Neumeier, Vienna (AT); Wolfgang Teschner, Vienna (AT); Leopold Bruckschwaiger, Altmunster (AT); Lucia Gnauer, Ebersbrunn (AT); Brigitte Talir, Biedermannsdorf (AT); Sandra Grand, Korneuburg (AT); Geoffrey Pot, Ronse (BE)

(73) Assignee: Takeda Pharmaceutical Company Limited, Osaka (JP)

( * ) Notice: Subject to any disclaimer, the term of this patent is extended or adjusted under 35 U.S.C. 154(b) by 909 days.

(21) Appl. No.: 17/907,536

(22) PCT Filed: Mar. 29, 2021

(86) PCT No.: PCT/US2021/024644
§ 371 (c)(1),
(2) Date: Sep. 27, 2022

(87) PCT Pub. No.: WO2021/202373
PCT Pub. Date: Oct. 7, 2021

(65) Prior Publication Data

US 2023/0142480 A1 May 11, 2023

Related U.S. Application Data

(60) Provisional application No. 63/002,791, filed on Mar. 31, 2020.

(51) Int. Cl.
*C07K 16/06* (2006.01)

(52) U.S. Cl.
CPC ........ *C07K 16/065* (2013.01); *C07K 2317/10* (2013.01)

(58) Field of Classification Search
CPC . C07K 14/70503; C07K 16/065; C07K 16/00
See application file for complete search history.

(56) References Cited

U.S. PATENT DOCUMENTS

| | | | |
|---|---|---|---|
| 5,886,154 | A | 3/1999 | Lebing et al. |
| 6,069,236 | A | 5/2000 | Burnouf-Radosevich et al. |
| 6,093,324 | A | 7/2000 | Bertolini et al. |
| 6,835,379 | B2 | 12/2004 | Andersson et al. |
| 7,186,410 | B2 | 3/2007 | Chtourou et al. |
| 7,553,938 | B2 | 6/2009 | Buchacher et al. |
| 8,841,248 | B2 | 9/2014 | Bairstow et al. |
| 8,993,734 | B2 | 3/2015 | Bruckschwaiger et al. |
| 2014/0271669 | A1 | 9/2014 | Hofbauer et al. |
| 2017/0073396 | A1 | 3/2017 | Bataille et al. |

FOREIGN PATENT DOCUMENTS

| | | | |
|---|---|---|---|
| AU | 2011244947 | A1 * | 12/2011 |
| JP | 2013-527201 | A | 6/2013 |
| JP | 2013-528183 | A | 7/2013 |
| JP | 2013-535468 | A | 9/2013 |
| WO | WO 2000034453 | A1 | 6/2000 |
| WO | WO 2001046219 | A2 | 6/2001 |
| WO | WO 2005073252 | A1 | 8/2005 |
| WO | WO 2011150284 | A2 | 12/2011 |
| WO | WO 2013/041677 | A1 | 3/2013 |
| WO | WO 2014113659 | A1 | 7/2014 |
| WO | WO 2015/136217 | A1 | 9/2015 |

OTHER PUBLICATIONS

Yao et al., Front Med., 2025; 12(1568333):1-10. (Year: 2025).*
Baylor College of Medicine—The Texas Heart Institute; Anticoagulants; https://www.texasheart.org/heart-health/heart-information-center/topics/anticoagulants/ (Year: 2025).*
Cober et al., Transfusion, 2001; 41: 1606-1609 (Year: 2001).*
Alving, B M et al. "Contact-activated factors: contaminants of immunoglobulins preparations with coagulant and vasoactive properties." The Journal of laboratory and clinical medicine vol. 96,2 (1980): 334-46.
Etscheid, M et al. "Identification of kallikrein and FXla as impurities in therapeutic immunoglobulins: implications for the safety and control of intravenous blood products." Vox sanguinis vol. 102,1 (2012): 40-6. doi:10.1111/j.1423-0410.2011.01502.x.
Hamamoto, Y et al. "A novel method for removal of human immunodeficiency virus: filtration with porous polymeric membranes." Vox sanguinis vol. 56,4 (1989): 230-6. doi:10.1111/j.1423-0410.1989.tb02034.x.
Horowitz, B et al. "Viral safety of solvent/detergent-treated blood products." Blood coagulation & fibrinolysis : an international journal in haemostasis and thrombosis vol. 5 Suppl 3 (1994): S21-8; discussion S29-S30. doi:10.1097/00001721-199412003-00006.
International Search Report and Written Opinion from International Application No. PCT/US2021/024644 issued on Oct. 7, 2021, 9 pages.
Kempf, C et al. "Virus inactivation during production of intravenous immunoglobulin." Transfusion vol. 31,5 (1991): 423-7. doi:10.1046/j.1537-2995.1991.31591263197.x.
Kreil, Thomas R et al. "West Nile virus and the safety of plasma derivatives: verification of high safety margins, and the validity of predictions based on model virus data." Transfusion vol. 43,8 (2003): 1023-8. doi:10.1046/j.1537-2995.2003.00496.x.

(Continued)

*Primary Examiner* — Brian Gangle
*Assistant Examiner* — Lakia J Jackson-Tongue
(74) *Attorney, Agent, or Firm* — Morgan, Lewis & Bockius LLP

(57) ABSTRACT

Described is a method for preparing an Immunoglobulin G (IgG) enriched fraction from a C1-INH depleted plasma supernatant. Isolation of Immunoglobulin G (IgG) enriched fraction from a C1-INH depleted plasma supernatant provided an alternative starting material for the manufacturing process. In the present invention, C1-INH depleted plasma supernatant is treated with heparin before further processing.

23 Claims, No Drawings

(56) References Cited

OTHER PUBLICATIONS

Louie, R E et al. "Inactivation of hepatitis C virus in low pH intravenous immunoglobulin." Biologicals : journal of the International Association of Biological Standardization vol. 22,1 (1994): 13-9. doi:10.1006/biol.1994.1003.

Pelletier, J P R et al. "Pathogen inactivation techniques." Best practice & research. Clinical haematology vol. 19,1 (2006): 205-42. doi:10.1016/j.beha.2005.04.001.

Wolberg, A S et al. "Coagulation factor XI is a contaminant in intravenous immunoglobulin preparations." American journal of hematology vol. 65,1 (2000): 30-4. doi:10.1002/1096-8652(200009)65:1<30::aid-ajh5>3.0.co;2-j.

Yuasa, T et al. "The particle size of hepatitis C virus estimated by filtration through microporous regenerated cellulose fibre." The Journal of general virology vol. 72 ( Pt 8) (1991): 2021-4. doi:10.1099/0022-1317-72-8-2021.

* cited by examiner

METHOD TO PRODUCE AN IMMUNOGLOBULIN PREPARATION FROM C-1 INHIBITOR DEPLETED PLASMA

CROSS REFERENCE TO RELATED APPLICATIONS

This application is a 317 national stage application based on International Application No. PCT/US2021/024644, filed Mar. 29, 2021, which claims priority to U.S. Provisional Patent Application Ser. No. 63/002,791, filed Mar. 31, 2020, the contents of which are hereby incorporated by reference in their entirety.

BACKGROUND OF THE INVENTION

Plasma-derived blood products are used to treat not only a variety of blood disorders, but diseases of other origin. For example, immune globulin (IgG) products from human plasma were first used in 1952 to treat immune deficiency. Since then, IgG preparations have found widespread use in at least three main categories of medical conditions: (1) immune deficiencies such as X-linked agammaglobulinemia, hypogammaglobulinemia (primary immune deficiencies), and acquired compromised immunity conditions (secondary immune deficiencies), featuring low antibody levels; (2) inflammatory and autoimmune diseases; and (3) acute infections.

While IVIG treatment can be very effective for managing primary immunodeficiency disorders, this therapy is only a temporary replacement for antibodies that are not being produced in the body, rather than a cure for the disease. Accordingly, patients dependent upon IVIG therapy require repeated doses, typically about once a month for life. This need places a great demand on the continued production of IVIG compositions. However, unlike other biologics that are produced via in vitro expression of recombinant DNA vectors, IVIG is fractionated from human blood and plasma donations. Thus, IVIG products cannot be increased by simply increasing the volume of production. Rather the level of commercially available IVIG is limited by the available supply of blood and plasma donations.

A number of IVIG preparation methods are used by commercial suppliers of IVIG products. One common problem with the current IVIG production methods is the substantial loss of IgG during the purification process, estimated to be at least 30% to 35% of the total IgG content of the starting material. One challenge is to maintain the quality of viral inactivation and lack of impurities which can cause adverse reactions, while bolstering the yield of IgG.

At the current production levels of IVIG, what may be considered small increases in the yield are in fact highly significant. For example at 2007 production levels, a 2% increase in efficiency, equal to an additional 56 milligrams per liter, would generate 1.5 additional metric tons of IVIG.

Various safety precautions must be taken into consideration when manufacturing and formulating plasma-derived biologic therapies. These include methods for removing and/or inactivating blood borne pathogens (e.g., viral and bacterial pathogens), anticomplement activity, and other unwanted contaminants arising from the use of donated plasma. Studies have suggested that administration of high levels of amidolytic activity may result in unwanted thromboembolic events (Wolberg A S et al., Coagulation factor XI is a contaminant in intravenous immunoglobulin preparations. Am J Hematol 2000; 65:30-34; and Alving B M et al., Contact-activated factors: contaminants of immunoglobulins preparations with coagulant and vasoactive properties. J Lab Clin Med 1980; 96:334-346; the disclosures of which are hereby incorporated by reference in their entireties for all purposes).

Highlighting this concern was the recent voluntary withdrawal of Octagam® (Octapharma) in the US and suspension of marketing authorization for Octagam® and Octagam 10% by the European Commission following increased reports of thromboembolic events. It is likely that the increased thrombolic events were caused by high levels of amidolytic activity in the biologic, caused by serine protease and serine protease zymogen impurities, such as Factor XI, Factor XIa, Factor XII and Factor XIIa (FDA Notice: Voluntary Market Withdrawal—Sep. 23, 2010 Octagam [Immune Globulin Intravenous (Human)] 5% Liquid Preparation; Octagam 50 mg/ml, solution—Octapharma France—Mise en quarantaine de tous les lots, published online Sep. 9, 2010 by the AFSSAPS; and Questions and answers on the suspension of the marketing authorisations for Octagam (human normal immunoglobulin 5% and 10%), published online Sep. 23, 2010 by the European Medicines Agency).

WO2014113659A1 discloses a method for isolating one or more blood products from an inter-alpha inhibitor protein (IαIp)-depleted blood product material. The blood product is isolated chromatographically from the IαIp-depleted cryo-poor plasma by contacting said IαIp-depleted cryo-poor plasma to a DEAE support. This reference does not disclose use of a C1-INH depleted plasma supernatant for the manufacture of IgG. It also fails to disclose treating plasma supernatant with heparin, thereby reducing the amidolytic and pro-coagulant activities in the IgG.

Due to rising concerns over the limited supply of starting material for the IgG preparation and loss of a significant amount of IgG during the purification process, there exist an immediate need in the art to provide a method to increase the availability of a significant amount of alternative starting material for the manufacturing of IgG.

BRIEF SUMMARY OF THE INVENTION

The present invention solves these and other problems. In one embodiment, the present invention is based on the finding that C1-INH depleted plasma supernatant can be used as a starting material for the preparation of Immunoglobulin G (IgG) enriched fraction, thus, making availability of another starting material for the preparation of IgG. Recent concerns over the amidolytic content of these compositions paired with the occurrence of thromboembolic events in patients being administered plasma-derived protein compositions, has highlighted a need in the art for a method for reducing serine proteases (e.g., FXIa and FXIIa) and serine protease zymogens (e.g., FXI and FXII) during the manufacturing of these biologics. Advantageously, the present invention is based, at least in part, on the surprising finding that heparin can be used to reduce the procoagulant and amidolytic activities to acceptable levels during the fractionation process. Also provided are therapeutic plasma-derived protein compositions having reduced serine protease activity, serine protease content, and/or serine protease zymogen content. Also provided are methods for treating or preventing disease by the administration of a composition of the invention.

In one embodiment, the present invention provides a method for preparing an Immunoglobulin G (IgG) enriched fraction from a C1-INH depleted supernatant fraction comprising IgG. The method includes:

(a) contacting the C1-INH depleted supernatant fraction with heparin, thereby forming a heparinized C1-INH depleted fraction; and (b) isolating IgG from the heparinized C1-INH depleted fraction, thereby forming an IgG enriched fraction.

In one embodiment of the methods described herein, the supernatant fraction is a supernatant produced following C1-inhibitor adsorption.

In an exemplary embodiment, the supernatant fraction is a plasma supernatant.

In one embodiment, the plasma supernatant is a C1-INH depleted cryo-poor plasma.

In various embodiments, the plasma supernatant is derived from a double-depleted cryo-poor plasma (DDCPP).

In an exemplary embodiment, the supernatant fraction is depleted of one or more other blood coagulation factor(s) selected from Factor II, VII, IX, X and a mixture thereof.

In one embodiment, the supernatant fraction is concentrated to a protein value of normal plasma before further processing.

In an exemplary embodiment, the heparin is added in an amount of from about 1 to about 20 Units per mL of supernatant fraction.

In an exemplary embodiment, the heparin is added in an amount of from about 5 to about 10 Units per mL of supernatant fraction.

In one embodiment, the heparin is added in an amount of about 5 Units per mL of supernatant fraction.

In various embodiments, the heparin is added in an amount of about 10 Units per mL of supernatant fraction.

In some embodiments, the method further comprises:

(c) removing C1-INH esterase inhibitor (C1-INH) from a cryo-poor plasma fraction containing C1-INH, thereby forming a C1-INH depleted supernatant fraction.

In one embodiment, the IgG enriched fraction contains from about 60% to about 80% of the IgG content found in the supernatant fraction.

In one embodiment, the IgG enriched fraction contains at least about 50% of the IgG content found in the supernatant fraction.

In one embodiment of the methods described above, the purity of γ-globulins in the IgG enriched fraction is at least about 95%.

In one embodiment of the methods described above, the purity of γ-globulins in the IgG enriched fraction is from about 95% to about 99.9%.

In an exemplary embodiment, the present invention provides a method for isolating IgG from the heparinized fraction comprising one or more of the following steps in any order or combination:

(i) precipitating the heparinized fraction with from about 6% to about 10% ethanol, e.g., aqueous ethanol, at a pH of from about 7.0 to about 7.5 to obtain a Fraction I precipitate and a Fraction I supernatant; and (ii) precipitating IgG from the Fraction I supernatant with from about 18% to about 27% ethanol, e.g., aqueous ethanol, at a pH of from about 6.7 to about 7.3 to form a Fraction II+III precipitate.

In one embodiment of the methods described above, the method further comprises precipitating IgG from the heparinized fraction with from about 18% to about 27% ethanol, e.g., aqueous ethanol, at a pH of from about 6.7 to about 7.3 to form a Fraction I+II+III precipitate.

In one embodiment, the method further comprises one or more of the following steps in any order or combination:

(iii) suspending the Fraction II+III or Fraction I+II+III precipitate in a suspension buffer, thereby forming an IgG suspension;

(iv) mixing finely divided silicon dioxide ($SiO_2$) with the IgG suspension, e.g., for at least about 30 minutes;

(v) filtering the IgG suspension, thereby forming a filtrate and a filter cake.

In one embodiment, the method further comprises one or more of the following steps in any order or combination:

(vi) washing the filter cake with at least about 1 filter press dead volume of a wash buffer having a pH of from about 4.9 to about 5.3, thereby forming a wash solution;

(vii) combining the filtrate with the wash solution, thereby forming a combined solution, and treating the combined solution with a detergent;

(viii) adjusting the pH of the combined solution of step (vii) to about 7.0 and adding thereto ethanol to a final concentration of from about 20% to about 30%, thereby forming a Precipitate G precipitate;

(ix) dissolving the Precipitate G precipitate in an aqueous solution comprising a member selected from a solvent, a detergent and a combination thereof, and incubating the solution, e.g., for at least about 60 minutes, forming an incubated solution;

(x) passing the incubated solution through a cation exchange chromatography column and eluting proteins absorbed on the column in an eluate;

(xi) passing the eluate through an anion exchange chromatography column to generate a flow-through fraction;

(x) passing the flow through fraction through a nanofilter to generate a nanofiltrate;

(xi) concentrating the nanofiltrate by ultrafiltration to generate a first ultrafiltrate;

(xii) diafiltering the first ultrafiltrate against a diafiltration buffer to generate a diafiltrate; and (xiii) concentrating the diafiltrate by ultrafiltration to generate a second ultrafiltrate having a protein concentration of from about 8% (w/v) to about 22% (w/v), thereby forming an IgG enriched fraction.

In one embodiment, the method comprises adding $SiO_2$ to a final concentration of from about 0.02 to about 0.10 grams of $SiO_2$ per gram of the Fraction II+III or Fraction I+II+III precipitate.

In one embodiment, the method comprises washing the filter cake with at least about 3 filter press dead volumes of a wash buffer.

In one embodiment, the method comprises washing the filter cake with at least about 2 filter press dead volumes of a wash buffer.

In one embodiment, the method comprises eluting at least one protein with at least about 35 mM sodium dihydrogen phosphate dihydrate.

In one embodiment, the diafiltration buffer comprises from about 200 mM to about 300 mM glycine.

In one embodiment, the method further comprises treating an IgG solution with a solvent and/or detergent in at least one viral inactivation or removal step.

In one embodiment of the methods described above, the method further comprises an incubation step at low pH, from about 4.0 to about 5.2.

In one embodiment of the methods described above, the method further comprises an incubation step at low pH, from about 4.4 to about 4.9.

In an exemplary embodiment, the present invention provides a supernatant after C1-inhibitor adsorption fraction comprising IgG, wherein said fraction is a cryo-poor plasma fraction depleted of C1-INH by at least about 70% of total present in the cryo-poor plasma fraction.

In a fourth aspect, the present invention provides a pharmaceutical composition comprising an IgG enriched fraction prepared according to the present invention.

In one embodiment, the composition comprises at least about 80 to 220 grams of IgG per liter of the composition.

In one embodiment, the pH of the pharmaceutical composition is from about 4.4 to about 4.9.

DETAILED DESCRIPTION OF THE INVENTION

A. Introduction

Unlike other biologics that are produced via recombinant expression of DNA vectors in host cell lines, plasma-derived proteins are fractionated from human blood and plasma donations. Thus, the supply of these products cannot be increased by simply increasing the volume of production. Rather the level of commercially available blood products is limited by the available supply of blood and plasma donations. This dynamic results in a shortage in the availability of raw human plasma for the manufacture of new plasma-derived blood factors that have lesser established commercial markets, including Complement Factor H (CFH) and inter-alpha-trypsin inhibitor proteins (IαIp).

Concerns over the amidolytic content of plasma-derived compositions has highlighted a need in the art for a method for reducing serine proteases (e.g., FXIa and FXIIa) and serine protease zymogens (e.g., FXI and FXII) during manufacturing of IgG, and other biologics.

C1-inhibitor (C1-INH, C1 esterase inhibitor) is the most important physiological inhibitor of plasma kallikrein, Factor XIa and Factor XIIa. Depletion of C1-inhibitor can result in accumulation of these factors in starting materials for the manufacture of commercial IgG therapeutics such as GAMMAGARD® LIQUID (GGL), making it challenging to produce IgG preparations for intravenous administration without elevated risk of thromboembolic events. Due to the complexity of the production of immunoglobulins from plasma supernatants after adsorption of C1-inhibitor, termed as double depleted cryo-poor plasma (DDCPP), the native plasma supernatant is not used as a starting material for the manufacture of IgG. Thus, to ensure the adequate removal of plasma kallikrein, Factor XIa and Factor XIIa with a reduced concentration of the C1-inhibitor, a calculated amount of 10,000 IU/L heparin is added to DDCPP before the alcohol fractionation process is initiated.

The present disclosure is based in part on the discovery that C1-INH depleted plasma supernatant as well as the supernatant fraction depleted of one or more of other blood coagulation factors selected from Factor II, VII, IX and X and a mixture thereof can be used as a starting material for the preparation of Immunoglobulin G (IgG) enriched fraction, thus, making available another starting material for the preparation of IgG. Advantageously, the present invention is based, at least in part, on the surprising finding that heparin can be used to increase procoagulant activity reduction during the fractionation process.

To overcome these issues, the inventors have developed a process incorporating a purification step, e.g., an initial purification step, that co-precipitates C1-INH depleted plasma supernatant with heparin, thereby forming a heparinized fraction; and then isolating IgG from the heparinized fraction. Thus, heparin treated C1-INH depleted plasma supernatant can be used as a starting material for the preparation of an Immunoglobulin G (IgG) enriched fraction, providing a new starting material for the preparation of IgG.

In certain aspects, the present invention provides methods for IVIG manufacture with reduced procoagulant and amidolytic activities.

In some embodiments, the present invention provides IgG compositions prepared according to the improved manufacturing methods provided herein. Advantageously, these compositions are less expensive to prepare than commercial products currently available due to the improved yield afforded by the methods provided herein. Furthermore, these compositions are as pure, if not more pure, than compositions manufactured using commercial methods. Importantly, these compositions are suitable for use in IVIG therapy for immune deficiencies, inflammatory and autoimmune diseases, and acute infections. In one embodiment, the IgG composition is at or about 10% IgG for intravenous administration. In another embodiment, the IgG composition is at or about 20% for subcutaneous or intramuscular administration.

In various embodiments, the present invention provides pharmaceutical compositions and formulations of IgG compositions prepared from the C1-INH depleted plasma supernatant as provided herein. In certain embodiments, these compositions and formulations provide improved properties as compared to other IVIG compositions currently on the market. For example, in certain embodiments, the compositions and formulations provided herein are stable for an extended period of time.

In an exemplary embodiment, the present invention provides method for treating immune deficiencies, inflammatory and autoimmune diseases, and acute infections comprising the administration of an IgG composition prepared from the C1-INH depleted plasma supernatant. In various embodiments, the IgG composition is prepared by a method of the invention.

Exemplary methods for the production of a C1-INH esterase inhibitor (C1-INH)-containing composition may be found in WO2001046219A2, which describes the use of anion exchangers at an acid pH (i.e., below pH 7), to isolate C1-INH.

B. Definitions

As used herein, the term "Intravenous IgG" or "IVIG treatment" refers generally to a therapeutic method of intravenously, subcutaneously, or intramuscularly administering a pharmaceutical composition of IgG immunoglobulins to a patient for treating a condition such as immune deficiencies, inflammatory diseases, and autoimmune diseases, for example. The IgG immunoglobulins are typically pooled and prepared from plasma. Whole antibodies or fragments can be used. IgG immunoglobulins can be formulated in higher concentrations (e.g., greater than 10%) for subcutaneous administration, or formulated for intramuscular administration. This is particularly common for specialty IgG preparations which are prepared with higher than average titers for specific antigens (e.g., Rho D factor, pertussis toxin, tetanus toxin, botulism toxin, rabies, etc.). For ease of discussion, such subcutaneously or intramuscularly formulated IgG compositions are also included in the term "IVIG" in this application.

As used herein, the term "amidolytic activity" refers to the ability of a polypeptide to catalyze the hydrolysis of at least one peptide bond in another polypeptide. The amidolytic activity profile for an IgG immunoglobulin composition may be determined by assaying with various chromogenic substrates, with different specificities for proteases found in human plasma, including without limitation: PL-1 (broad spectrum), S-2288 (broad spectrum), S-2266 (FXIa, glandular kallikreins), S-2222 (FXa, trypsin), S-2251 (Plasmin), and S-2302 (Kallikrein, FXIa and FXIIa). Methods for determining the amidolytic activity of a composition are well known in the art, for example, as described in M. Etscheid et al. (Identification of kallikrein and FXIa as impurities in therapeutic immunoglobulins: implications for the safety and control of intravenous blood products, Vox Sang 2011; the disclosure of which is hereby expressly incorporated by reference in its entirety for all purposes.)

As used herein, an "antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. An exemplary immunoglobulin (antibody) structural unit is composed of two pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

As used herein, the term "ultrafiltration (UF)" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular ($10^3$-$10^6$ Da) solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar, and is particularly useful for separating colloids like proteins from small molecules like sugars and salts.

As used herein, the term "diafiltration" is performed with the same membranes as ultrafiltration and is a tangential flow filtration. During diafiltration, buffer is introduced into the recycle tank while filtrate is removed from the unit operation. In processes where the product is in the retentate (for example IgG), diafiltration washes components out of the product pool into the filtrate, thereby exchanging buffers and reducing the concentration of undesirable species.

As used herein, the term "about" denotes an approximate range from a specified value. In some embodiments, the range is plus or minus from 1%-10% from a specified value. Thus, "about" encompasses plus or minus, 1%, 2%, 3%, 4%, 5%, 6%, 7%, 8%, 9% and 10% from the stated value. For instance, the language "about 20%" encompasses a range of 18-22%.

As used herein, the term "solvent" encompasses any liquid substance capable of dissolving or dispersing one or more other substances. A solvent may be inorganic in nature, such as water, or it may be an organic liquid, such as ethanol, acetone, methyl acetate, ethyl acetate, hexane, petrol ether, etc. As used in the term "solvent detergent treatment," solvent denotes an organic solvent (e.g., tri-N-butyl phosphate), which is part of the solvent detergent mixture used to inactivate lipid-enveloped viruses in solution.

As used herein, the term "detergent" is used interchangeably with the term "surfactant" or "surface acting agent." Surfactants are typically organic compounds that are amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Long chain fatty acids and their salts: including caprylate, caprylic acid, heptanoat, hexanoic acid, heptanoic acid, nanoic acid, decanoic acid, and the like; Zwitterionic (amphoteric): dodecyl betaine; cocamidopropyl betaine; coco ampho glycinate; nonionic: alkyl poly(ethylene oxide), alkylphenol poly(ethylene oxide), copolymers of poly(ethylene oxide) and poly(propylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

As used in this application, the term "spraying" refers to a means of delivering a liquid substance into a system, e.g., during an alcohol precipitation step, such as a modified Cohn Fractionation I or II+III precipitation step, in the form of fine droplets or mist of the liquid substance. Spraying may be achieved by any pressurized device, such as a container (e.g., a spray bottle), that has a spray head or a nozzle and is operated manually or automatically to generate a fine mist from a liquid. Typically, spraying is performed while the system receiving the liquid substance is continuously stirred or otherwise mixed to ensure rapid and equal distribution of the liquid within the system.

As used herein, "cryo-poor plasma" refers to the supernatant formed after the cold precipitation (cryo-precipitation) of plasma or pooled plasma at temperatures nearing freezing, e.g., at temperatures below about 10° C. In the context of the present invention, plasma may refer interchangeably to recovered plasma (i.e., plasma that has been separated from whole blood ex vivo) or source plasma (i.e., plasma collected via plasmapheresis). Cryo-precipitation is commonly performed, for example, by thawing previously frozen pooled plasma, which has already been assayed for safety and quality considerations, although fresh plasma may also be used. Thawing is typically carried out at a temperature no higher than 6° C. After complete thawing of the frozen plasma at low temperature, centrifugation is performed in the cold (e.g., ≤6° C.) to separate solid cryo-precipitates from the liquid supernatant. Alternatively, the separation step can be performed by filtration rather than centrifugation.

As used herein, a "Cohn pool" refers to the starting material used for the fractionation of a plasma sample or pool of plasma samples. Cohn pools include whole plasma, cryo-poor plasma samples, and pools of cryo-poor plasma samples that may or may not have been subjected to a pre-processing step. In certain embodiments, a Cohn pool is a cryo-poor plasma sample from which one or more blood factors have been removed in a pre-processing step, for example, adsorption onto a solid phase (e.g., aluminum hydroxide, finely divided silicon dioxide, etc.), or chromatographic step (e.g., ion exchange or heparin affinity chromatography). Various blood factors, including but not limited to Factor Eight Inhibitor Bypass Activity (FEIBA), Factor IX-complex, Factor VII-concentrate, or Antithrombin III-complex, may be isolated from the cryo-poor plasma sample to form a Cohn pool.

As used herein, the term "plasma sample" refers to any suitable material, for example, recovered plasma or source plasma or plasma fractions or plasma supernatants or plasma derived protein preparations. An exemplary "plasma sample" includes an IgG derived from plasma or plasma fractions, an IgG derived from cryo-poor plasma, an IgG derived from a C- 1 esterase inhibitor adsorption of cryo-poor plasma, an IgG derived from a double-depleted cryo-poor plasma (DDCPP).

As used herein, the "double depleted cryo-poor plasma (also known as DDCPP/C-1 esterase inhibitor depleted cryo-poor plasma") refers to the adsorption supernatant formed after the adsorption of C1-inhibitor of cryo-poor plasma at temperatures nearing freezing, e.g., at temperatures below about 8° C. GAMMAGARD® LIQUID (Baxter Healthcare Corporation, Westlake Village, CA) manufacturing process employs a modified Cohn-Oncley cold ethanol fractionation procedure to isolate an intermediate immunoglobulin G (IgG) fraction, referred to as Precipitate G (PptG), from frozen human plasma pools. PptG is further purified through the subsequent use of weak cation and weak anion exchange chromatography. Three dedicated virus reduction steps are included in the downstream purification of PptG, which are solvent/detergent treatment, nanofiltration, and incubation at low pH and elevated temperature in the final formulation. The starting material for the ethanol fractionation process can undergo different adsorption steps to obtain intermediates for the purification of coagulation factors and plasma protein inhibitors. The adsorption supernatant obtained after the adsorption of C1-inhibitor in the CINRYZE® manufacturing process is termed as double depleted cryo-poor plasma (DDCPP).

As used herein, the term "native or variant native" refers to use of DDCPP as starting material without any adjustment/modification and "variant heparin" refers to the addition of 5000 IU heparin/L DDCPP or 10000 IU heparin/L DDCPP to the starting material. 'variant NaCl' refers to the addition of sodium chloride to increase the conductivity of the DDCPP.

As used herein, the term "C1-inhibitor (C1-inh, C1 esterase inhibitor)" is a protease inhibitor belonging to the serpin superfamily. Its main function is the inhibition of the complement system to prevent spontaneous activation. C1-inhibitor is an acute-phase protein that circulates in blood at levels of around 0.25 g/L. The levels rise ~2-fold during inflammation. C1-inhibitor irreversibly binds to and inactivates C1r and C1s proteases in the C1 complex of classical pathway of complement. MASP-1 and MASP-2 proteases in Mannose-binding lectin (MBL) complexes of the lectin pathway are also inactivated. This way, C1-inhibitor prevents the proteolytic cleavage of later complement components C4 and C2 by C1 and MBL. Although named after its complement inhibitory activity, C1-inhibitor also inhibits proteases of the fibrinolytic, clotting, and kinin pathways. Note that C1-inhibitor is the most important physiological inhibitor of plasma kallikrein, FXIa, and FXIIa.

1. Preparation of C1-INH Depleted Supernatant Fraction

The starting material used for preparing IgG enriched fraction generally consists of supernatant after the C1-inhibitor adsorption or frozen plasma after the C1-inhibitor adsorption or non-frozen plasma after the C1-inhibitor adsorption. An exemplary sample, e.g., a plasma supernatant, consists of the adsorption supernatant obtained after the adsorption of C1-inhibitor in the CINRYZE® manufacturing process. The purification process typically starts with thawing previously frozen pooled plasma, which preferably has already been assayed for safety and quality considerations. Thawing is typically carried out at a temperature no higher than 6° C. After complete thawing of the frozen plasma at low temperature, centrifugation is performed in the cold (e.g., ≤6° C.) to separate solid cryo-precipitates from the liquid supernatant. Alternatively, the separation step is performed by filtration rather than centrifugation. The liquid supernatant (also referred to as "cryo-poor plasma," after cold-insoluble proteins are removed by centrifugation from fresh thawed plasma) then undergoes one or more adsorption step to obtain intermediates for the purification of coagulation factors and plasma protein inhibitors. The adsorption supernatant obtained after the adsorption of C1-inhibitor from the cryo-poor plasma is also termed as double depleted cryo-poor plasma (DDCPP).

2. Preparation of Heparinized Fraction

C1-INH depleted supernatant fraction is generally not considered an ideal starting material for the manufacture of IgG as depletion of C1-INH results in accumulation of plasma kallikrein, Factor XIa, and Factor XIIa. To ensure the adequate removal of these factors with clearly reduced concentration of the C1-INH, a calculated amount of heparin (5000 U/kg DDCPP or 10,000 U/kg DDCPP) is added to the C1-INH depleted supernatant fraction before the alcohol fractionation process is initiated. The final IgG product obtained is shown to contain residual heparin concentrations of less than 1 IU/mL.

3. First Precipitation Event—Modified Fractionation I

The starting material for fractionation I was DDCPP (supernatant after C1-inhibitor adsorption). DDCPP is typically cooled to about 0±2° C. and the pH is adjusted to from about 7.0 to about 7.5, preferably from about 7.1 to about 7.3, most preferably about 7.2 by addition of acid, e.g., acetic acid. In one embodiment, the pH of the cryo-poor plasma is adjusted to a pH of about 7.2. Pre-cooled ethanol is then added while the plasma is stirred to a target concentration of ethanol at or about 8% v/v. At the same time the temperature is further lowered to from about −2° C. to about +2° C. In a preferred embodiment, the temperature is lowered to at or about −1.5° C., to precipitate contaminants such as $\alpha_2$-macroglobulin, $\beta_{1A}$- and $\beta_{1C}$-globulin, fibrinogen, and Factor VIII. Typically, the precipitation event will include a hold time of at least about 1 hour, although shorter or longer hold times may also be employed. Subsequently, the supernatant (Supernatant I), ideally containing the bulk of the IgG content present in the DDCPP, is then collected by centrifugation, filtration, or another suitable method.

As compared to conventional methods employed as a first fractionation step for cryo-poor plasma (Cohn et al., supra; Oncley et al., supra), the present invention provides, in several embodiments, methods that result in improved IgG yields from the Supernatant I fraction. In one embodiment, the improved IgG yield is achieved by adding the alcohol by spraying. In another embodiment, the improved IgG yield is achieved by adding a pH modifying agent by spraying. In yet another embodiment, the improved IgG yield is achieved by adjusting the pH of the solution after addition of the alcohol. In a related embodiment, the improved IgG yield is achieved by adjusting the pH of the solution during the addition of the alcohol.

In one specific aspect, the improvement relates to a method in which a reduced amount of IgG is lost in the precipitate fraction of the first precipitation step. For example, in certain embodiments, a reduced amount of IgG is lost in the precipitate fraction of the first precipitation step as compared to the amount of IgG lost in the first precipitation step of the Cohn method 6 protocol.

In certain embodiments, the process improvement is realized by adjusting the pH of the solution to from about 7.0 to about 7.5 after the addition of the precipitating alcohol. In other embodiments, the pH of the solution is adjusted to from about 7.1 to about 7.3 after addition of the precipitating alcohol. In yet other embodiments, the pH of the solution is adjusted to about 7.0 or about 7.1, 7.2, 7.3, 7.4, or 7.5 after addition of the precipitating alcohol. In a particular embodiment, the pH of the solution is adjusted to about 7.2 after addition of the precipitating alcohol. As such, in certain embodiments, a reduced amount of IgG is lost in the precipitate fraction of the first precipitation step as compared to an analogous precipitation step in which the pH of the solution is adjusted prior to but not after addition of the precipitating alcohol. In one embodiment, the pH is maintained at the desired pH during the precipitation hold or incubation time by continuously adjusting the pH of the solution. In one embodiment, the alcohol is ethanol.

In other certain embodiments, the process improvement is realized by adding the precipitating alcohol and/or the solution used to adjust the pH by spraying, rather than by fluent addition. As such, in certain embodiments, a reduced amount of IgG is lost in the precipitate fraction of the first precipitation step as compared to an analogous precipitation step in which the alcohol and/or solution used to adjust the pH is introduced by fluent addition. In one embodiment, the alcohol is ethanol.

In yet other certain embodiments, the improvement is realized by adjusting the pH of the solution to between about 7.0 and about 7.5. In a preferred embodiment, the pH of the solution is adjusted to between about 7.1 and about 7.3. In other embodiments, the pH of the solution is adjusted to about 7.0, 7.1, 7.2, 7.3, 7.4, or 7.5 after the addition of the precipitating alcohol and by adding the precipitating alcohol and/or the solution used to adjust the pH by spraying, rather than by fluent addition. In a particular embodiment, the pH of the solution is adjusted to about 7.2 after addition of the precipitating alcohol and by adding the precipitating alcohol and/or the solution used to adjust the pH by spraying, rather than by fluent addition. In one embodiment, the alcohol is ethanol.

4. Second Precipitation Event—Modified Fractionation II+III

To further enrich the IgG content and purity of the fractionation, Supernatant I is subjected to a second precipitation step, which is a modified Cohn-Oncley Fraction II+III fractionation. Generally, the pH of the solution is adjusted to a pH of from about 6.6 to about 6.8. In a preferred embodiment, the pH of the solution is adjusted to about 6.7. Alcohol, preferably ethanol, is then added to the solution while being stirred to a final concentration of from about 20% to about 25% (v/v) to precipitate the IgG in the fraction. In a preferred embodiment, alcohol is added to a final concentration of about 25% (v/v) to precipitate the IgG in the fraction. Generally, contaminants such as $\alpha_1$-lipoprotein, $\alpha_1$-antitrypsin, Gc-globulins, $\alpha_{1X}$-glycoprotin, haptoglobulin, ceruloplasmin, transferrin, hemopexin, a fraction of the Christmas factor, thyroxin binding globulin, cholinesterase, hypertensinogen, and albumin will not be precipitated by these conditions.

Prior to or concomitant with alcohol addition, the solution is further cooled to between about −7° C. and about −9° C. In a preferred embodiment, the solution is cooled to a temperature of about −7° C. After completion of the alcohol addition, the pH of the solution is immediately adjusted to from about 6.8 to about 7.0. In a preferred embodiment, the pH of the solution is adjusted to about 6.9. Typically, the precipitation event will include a hold time of at least about 10 hours, although shorter or longer hold times may also be employed. Subsequently, the precipitate (Modified Fraction II+III), which ideally contains at least about 85%, preferably at least about 90%, more preferably at least about 95%, of the IgG content present in the cryo-poor plasma, is separated from the supernatant by centrifugation, filtration, or another suitable method and collected. As compared to conventional methods employed as a second fractionation step for cryo-poor plasma (Cohn et al., supra; Oncley et al., supra), the present invention provides, in several embodiments, methods that result in improved IgG yields in the Modified Fraction II+III precipitate. In a related embodiment, the present invention provides methods that result in a reduced loss of IgG in the Modified II+III supernatant.

As compared to conventional methods employed as a second fractionation step for cryo-poor plasma (Cohn et al., supra; Oncley et al., supra), the present invention provides, in several embodiments, methods that result in improved IgG yields in the Modified Fraction II+III precipitate. In one embodiment, the improvement is realized by the addition of alcohol by spraying. In another embodiment, the improvement is realized by the addition of a pH modifying agent by spraying. In another embodiment, the improvement is realized by adjusting the pH of the solution after addition of the alcohol. In a related embodiment, the improvement is realized by adjusting the pH of the solution during addition of the alcohol. In another embodiment, the improvement is realized by increasing the concentration of alcohol (e.g., ethanol) to about 25% (v/v). In another embodiment, the improvement is realized by lowering the temperature of the precipitation step to from about −7° C. to about −9° C. In a preferred embodiment, the improvement is realized by increasing the concentration of alcohol (e.g., ethanol) to about 25% (v/v) and lowing the temperature to from about −7° C. to about −9° C. In comparison, both Cohn et al. and Oncley et al. perform precipitation at −5° C. and Oncley et al. use 20% alcohol, in order to reduce the level of contaminants in the precipitate. Advantageously, the methods provided herein allow for maximal IgG yield without high levels of contamination in the final product.

It has been discovered that when the pH of the solution is adjusted to a pH of about 6.9 prior to addition of the precipitating alcohol, the pH of the solution shift from 6.9 to from about 7.4 to about 7.7, due in part to protein precipitation. As the pH of the solution shifts away from 6.9, precipitation of IgG becomes less favorable and the precipitation of certain contaminants becomes more favorable. Advantageously, the inventors have found that by adjusting the pH of the solution after addition of the precipitating alcohol, that a higher percentage of IgG is recovered in the Fraction II+III precipitate.

In various embodiments, the improvement realized by the invention relates to a method in which a reduced amount of IgG is lost in the supernatant fraction of the modified Fraction II+III precipitation step when compared to an identical method in which the improvement of the invention is not incorporated. In other words, an increased percentage of the starting IgG is present in the Fraction II+III precipitate. In certain embodiments, the process improvement is realized by adjusting the pH of the solution to from about 6.7 to about 7.1 immediately after or during the addition of the precipitating alcohol. In some embodiment, the process improvement is realized by maintaining the pH of the solution from about 6.7 to about 7.1 continuously during the precipitation and/or incubation period. In some embodiments, the pH of the solution is adjusted to from about 6.8 to about 7.0 immediately after or during the addition of the precipitating alcohol, or to a pH of about 6.7, 6.8, 6.9, 7.0, or 7.1 immediately after or during the addition of the precipitating alcohol. In a particular embodiment, the pH of the solution is adjusted to about 6.9 immediately after or during the addition of the precipitating alcohol. In certain embodiments, the pH of the solution is maintained at from about 6.8 to about 7.0 continuously during the precipitation incubation period, or at a pH of about 6.9 continuously during the precipitation incubation period. Applying the process parameters of the invention, in certain embodiments, a reduced amount of IgG is lost in the supernatant fraction of the second precipitation step as compared to an analogous precipitation step in which the pH of the solution is adjusted prior to but not after addition of the precipitating alcohol or to an analogous precipitation step in which the pH of the solution is not maintained during the entirety of the precipitation incubation period. In one embodiment, the pH is maintained at the desired pH during the precipitation hold or incubation time by continuously adjusting the pH of the solution. In one embodiment, the alcohol is ethanol.

In some embodiments, the process improvement is realized by adding the precipitating alcohol and/or the solution used to adjust the pH by spraying, rather than by fluent addition. As such, in certain embodiments, a reduced amount of IgG is lost in the supernatant fraction of the second precipitation step as compared to an analogous precipitation step in which the alcohol and/or solution used to adjust the pH is introduced by bulk, fluent addition. In one embodiment, the alcohol is ethanol.

In another embodiment, the process improvement is realized by performing the precipitation step at a temperature from about −7° C. to about −9° C. In one embodiment, the precipitation step is performed at a temperature of about −7° C. In an exemplary embodiment, the precipitation step is performed at a temperature of about −8° C. In various embodiments, the precipitation step is performed at a temperature of about −9° C. In certain embodiments, the alcohol concentration of the precipitation step is between about 23% and about 27%. In a preferred embodiment, the alcohol concentration is between about 24% and about 26%. In an exemplary embodiment, the alcohol concentration is about 25%. In some embodiments, the alcohol concentration may be at or about 23%, 24%, 25%, 26%, or 27%. In an exemplary embodiment, the second precipitation step is performed at a temperature of at or about −7° C. with an alcohol concentration of about 25%. In one embodiment, the alcohol is ethanol.

The effect of increasing the alcohol concentration in the second precipitation from 20%, as used in Oncley et al., supra, to 25% and lowering the temperature of the incubation from −5° C., as used in the Cohn and Oncley methods, to about −7° C. is a surprising 5% to 6% increase in the IgG content of the modified Fraction II+III precipitate.

In another embodiment, the process improvement is realized by adjusting the pH of the solution to between about 6.7 and about 7.1, preferably at or about 6.9, immediately after or during the addition of the precipitating alcohol, maintaining the pH of the solution at a pH of between about 6.7 and about 7.1, preferably at or about 6.9, by continuously adjusting the pH during the precipitation incubation period, and by adding the precipitating alcohol and/or the solution used to adjust the pH by spraying, rather than by fluent addition.

In an exemplary embodiment, the process improvement is realized by performing the precipitation step at a temperature between about −7° C. and about −9° C., e.g., −7° C. and by precipitating the IgG with an alcohol concentration of from about 23% to about 27%, e.g., at 25%. In various embodiments, the process improvement is realized by incorporating all of the Modified Fraction II+III improvements provided above into a process. In an exemplary embodiment, the process improvement is realized by precipitating IgG at a temperature of −7° C. with 25% ethanol added by spraying and then adjusting the pH of the solution to 6.9 after addition of the precipitating alcohol. In yet another preferred embodiment, the pH of the solution is maintained at 6.9 for the entirety of the precipitation incubation or hold time.

5. Extraction of the Modified Fraction II+III Precipitate

In order to solubilize the IgG content of the modified Fraction II+III precipitate, a cold extraction buffer is used to re-suspend the Fractionation II+III precipitate at a ratio of about 1 part precipitate to about 15 parts of extraction buffer. Other suitable re-suspension ratios may be used, for example, from about 1:8 to about 1:30, e.g., from about 1:10 to about 1:20, from about 1:12 to about 1:18, from about 1:13 to about 1:17, from about 1:14 to about 1:16. In certain embodiments, the re-suspension ratio may be about 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, or higher.

Suitable solutions for the extraction of the modified II+III precipitate generally have a pH between about 4.0 and about 5.5. In certain embodiments, the solution has a pH from about 4.5 to about 5.0. In some embodiments, the extraction solution has a pH of about 4.0, 4.1, 4.2, 4.3, 4.4, 4.5, 4.6, 4.7, 4.8, 4.9, 5.0, 5.1, 5.2, 5.3, 5.4, or 5.5. In an exemplary embodiment, the pH of the extraction buffer is about 4.5. In an exemplary embodiment, the pH of the extraction buffer is about 4.7. In an exemplary embodiment, the pH of the extraction buffer will be about 4.9. Generally, these pH requirements can be met using a buffering agent selected from, for example, acetate, citrate, monobasic phosphate, dibasic phosphate, mixtures thereof, and the like. Suitable buffer concentrations typically range from about 5 to about 100 mM, or from about 10 to about 50 mM, or about 5, 10, 15, 20, 25, 30, 35, 40, 45, 50, 55, 60, 65, 70, 75, 80, 85, 90, 95, or 100 mM buffering agent.

Exemplary extraction buffers have a conductivity of from about 0.5 $mS \cdot cm^{-1}$ to about 2.0 $mS \cdot cm^{-1}$. For example, in certain embodiments, the conductivity of the extraction buffer is about 0.5 $mS \cdot cm^{-1}$, or about 0.6, 0.7, 0.8, 0.9, 1.0, 1.1, 1.2, 1.3, 1.4, 1.5, 1.6, 1.7, 1.8, 1.9, or about 2.0 $mS \cdot cm^{-1}$. One of ordinary skill in the art will know how to generate extraction buffers having an appropriate conductivity.

In one particular embodiment, an exemplary extraction buffer may about 5 mM monobasic sodium phosphate and about 5 mM acetate at a pH of about 4.5±0.2 and conductivity of about 0.7 to 0.9 mS/cm.

Generally, the extraction is performed at between about 0° C. and about 10° C., or between about 2° C. and about 8° C. In certain embodiments, the extraction may be performed at about 0° C., 1° C., 2° C., 3° C., 4° C., 5° C., 6° C., 7° C., 8° C., 9° C., or 10° C. In an exemplary embodiment, the extraction is performed at from about 2° C. to about 10° C. Typically, the extraction process will proceed for from about 60 to about 300 minutes, or for from about 120 to about 240 min, or from about 150 to about 210 minutes, while the suspension is continuously stirred. In certain embodiments, the extraction process will proceed for about 60, 70, 80, 90, 100, 110, 120, 130, 140, 150, 160, 170, 180, 190, 200, 210, 220, 230, 240, 250, 260, 270, 280, 290, or about 300 minutes. In a preferred embodiment, the extraction process will proceed for at least about 160 minutes with continuous stirring.

It has been found that in methods employing an extraction buffer containing 5 mM monobasic sodium phosphate, 5 mM acetate, and 0.051% to 0.06% glacial acetic acid (v/v), a substantial increase in the yield increase in the final IgG composition can be obtained without jeopardizing the purity of the final product. In a preferred embodiment, the Fraction II+III precipitate is extracted with a paste to buffer ratio of at or about 1:15 at a pH of at or about 4.5±0.2.

Advantageously, it has been found that compared to the current manufacturing process for GAMMAGARD® LIQUID (Baxter Healthcare), which employs an extraction buffer containing 5 mM monobasic sodium phosphate, 5 mM acetate, and 0.051% glacial acetic acid (v/v), that by increasing the glacial acetic acid content to at or about 0.06% (v/v), a substantial increase in the yield increase in the final IgG composition can be obtained. As compared to methods previously employed for the extraction of the precipitate formed by the second precipitation step (GAMMAGARD® LIQUID), the present invention provides, in several embodiments, methods that result in improved IgG yields in the Modified Fraction II+III suspension.

In one embodiment, the improvement relates to a method in which a reduced amount of IgG is lost in the non-solubilized fraction of the Modified Fraction II+III precipitate. In one embodiment, the process improvement is realized by extracting the Modified Fraction II+III precipitate at a ratio of 1:15 (precipitate to buffer) with a solution containing 5 mM monobasic sodium phosphate, 5 mM acetate, and 0.06% glacial acetic acid (v/v). In another embodiment, the improvement is realized by maintaining the pH of the solution relatively constant during the duration of the extraction process. In one embodiment, the pH of the solution is maintained at from about 4.1 to about 4.9 for the duration of the extraction process. In an exemplary embodiment, the pH of the solution is maintained at from about 4.2 to about 4.8 for the duration of the extraction process. In some embodiments, the pH of the solution is maintained at from about 4.3 to about 4.7 for the duration of the extraction process. In various embodiments, the pH of the solution is maintained at from about 4.4 to about 4.6 for the duration of the extraction process. In some embodiments, the pH of the solution is maintained at 4.5 for the duration of the extraction process.

In an exemplary embodiment, the improvement relates to a method in which an increased amount of IgG is solubilized from the Fraction II+III precipitate in the Fraction II+III dissolution step. In one embodiment, the process improvement is realized by solubilizing the Fraction II+III precipitate in a dissolution buffer containing about 600 mL glacial acetic acid per about 1000 L. In another embodiment, the improvement relates to a method in which impurities are reduced after the IgG in the Fraction II+III precipitate is solubilized. In one embodiment, the process improvement is realized by mixing finely divided silicon dioxide ($SiO_2$) with the Fraction II+III suspension for at least about 30 minutes.

6. Pretreatment and Filtration of the Modified Fraction II+III Suspension

In order to remove the non-solubilized fraction of the Modified Fraction II+III precipitate (i.e., the Modified Fraction II+III filter cake), the suspension is filtered, typically using depth filtration. Depth filters that may be employed in the methods provided herein include, metallic, glass, ceramic, organic (such as diatomaceous earth) depth filters, and the like. Example of suitable filters include, without limitation, Cuno 50SA, Cuno 90SA, and Cuno VR06 filters (Cuno). Alternatively, the separation step can be performed by centrifugation rather than filtration.

Although the manufacturing process improvements described above minimize IgG losses in the initial steps of the purification process, critical impurities, including PKA activity, amidolytic activity, and fibrinogen content, are much higher when, for example, the II+III paste is extracted at pH 4.5 or 4.6, as compared to when the extraction occurs at a pH around 4.9 to 5.0.

In order to mitigate the impurities extracted in the methods provided herein, it has now been found that the purity of the IgG composition can be greatly enhanced by the addition of a pretreatment step prior to filtration/centrifugation. In one embodiment, this pretreatment step comprises addition of finely divided silica dioxide particles (e.g., fumed silica, Aerosil®). In an exemplary embodiment, this treatment is followed by a 40 to 80 minute incubation period during which the suspension is constantly mixed. In certain embodiments, the incubation period is between about 50 minutes and about 70 minutes. In various embodiment, the incubation period is about 30, 35, 40, 45, 50, 55, 60, 65, 70, 75, 80, or more minutes. Generally, the treatment will be performed at from about 0° C. to about 10° C., or from about 2° C. to about 8° C. In certain embodiments, the treatment may be performed at about 0° C., 1° C., 2° C., 3° C., 4° C., 5° C., 6° C., 7° C., 8° C., 9° C., or 10° C. In a particular embodiment, the treatment is performed at between about 2° C. and about 10° C.

The fumed silica treatment is exemplified in WO2011150284A2. In this patent application, a Fraction II+III precipitate is suspended and split into two samples, one of which is clarified with filter aid only prior to filtration and one of which is treated with fumed silica prior to addition of the filter aid and filtration. As can be seen in the chromatographs and in the quantitated data, the filtrate sample pretreated with fumed silica had a much higher IgG purity than the sample only treated with filter aid.

In certain embodiments, fumed silica is added at a concentration of from about 20 g/kg II+III paste to about 100 g/kg II+III paste (e.g., for a Modified Fraction II+III precipitate that is extracted at a ratio of 1:15, fumed silica should be added at a concentration from about 20 g/16 kg II+III suspension to about 100 g/16 kg II+III suspension, or at a final concentration of about 0.125% (w/w) to about 0.625% (w/w)). In certain embodiments, the fumed silica may be added at a concentration of about 20 g/kg II+III paste, or about 25, 30, 35, 40, 45, 50, 55, 60, 65, 70, 75, 80, 85, 90, 95, or 100 g/kg II+III paste. In one specific embodiment, fumed silica (e.g., Aerosil 380 or equivalent) is added to the Modified Fraction II+III suspension to a final concentration of about 40 g/16 kg II+III. Mixing takes place at about 2 to about 8° C. for at least about 50 to about 70 minutes.

In certain embodiments, $SiO_2$ is added to an IgG composition at a concentration from about 0.01 g/g protein to about 10 g/g protein. In another embodiment, $SiO_2$ is added to an IgG composition at a concentration from about 0.01 g/g protein to about 5 g/g protein. In another embodiment, $SiO_2$ is added to an IgG composition at a concentration between about 0.02 g/g protein and about 4 g/g protein. In one embodiment, $SiO_2$ is added at a final concentration of at least 0.1 g per gram total protein. In another specific embodiment, fumed silica is added at a concentration of at least 0.2 g per gram total protein. In another specific embodiment, fumed silica is added at a concentration of at least 0.25 g per gram total protein. In other specific embodiments, fumed silica is added at a concentration of at least 1 g per gram total protein. In another specific embodiment, fumed silica is added at a concentration of at least 2 g per gram total protein. In another specific embodiment, fumed silica is added at a concentration of at least 2.5 g per gram total protein. In yet other specific embodiments, finely divided silicon dioxide is added at a concentration of at least 0.01 g/g total protein or at least 0.02 g, 0.03 g, 0.04 g, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1.0 g, 1.5 g, 2.0 g, 2.5 g, 3.0 g, 3.5 g, 4.0 g, 4.5 g, 5.0 g, 5.5 g, 6.0 g, 6.5 g, 7.0 g, 7.5 g, 8.0 g, 8.5 g, 9.0 g, 9.5 g, 10.0 g, or more per gram total protein.

In certain embodiments, filter aid, for example Celpure C300 (Celpure) or Hyflo-Supper-Cel (World Minerals), is added after the silica dioxide treatment, to facilitate depth filtration. Filter aid can be added at a final concentration of from about 0.01 kg/kg II+III paste to about 1.0 kg/kg II+III paste, or from about 0.02 kg/kg II+III paste to about 0.8 kg/kg II+III paste, or from about 0.03 kg/kg II+III paste to about 0.7 kg/kg II+III paste. In other embodiments, filter aid can be added at a final concentration of from about 0.01 kg/kg II+III paste to about 0.07 kg/kg II+III paste, or from about 0.02 kg/kg II+III paste to about 0.06 kg/kg II+III paste, or from about 0.03 kg/kg II+III paste to about 0.05 kg/kg II+III paste. In certain embodiments, the filter aid will be added at a final concentration of about 0.01 kg/kg II+III paste, or about 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 kg/kg II+III paste.

In previous methods of purifying IgG, a significant fraction of IgG was being lost during the filtration step in the process. It was found that the standard methods of post-filtration wash, using 1.8 dead volumes of suspension buffer to purge the filter press frames and lines, were insufficient for maximal recovery of IgG at this step. Surprisingly, it was found that at least 3.0 dead volumes, e.g., 3.6 dead volumes, of suspension buffer were useful for efficient recovery of IgG in the Modified Fraction II+III clarified suspension. In certain embodiments, the filter press is washed with any suitable suspension buffer. In an exemplary embodiment, the wash buffer will comprise, for example, 5 mM monobasic sodium phosphate, 5 mM acetate, and 0.015% glacial acetic acid (v/v).

In one embodiment, the improvement relates to a method in which a reduced amount of IgG is lost during the Fraction II+III suspension filtration step. In one embodiment, the process improvement is realized by post-washing the filter with at least about 3.6 dead volumes of dissolution buffer containing 150 mL glacial acetic acid per 1000 L. In one embodiment, the pH of the post-wash extraction buffer is between about 4.6 and about 5.3. In a preferred embodiment, the pH of the post-wash buffer is between about 4.7 and about 5.2. In another preferred embodiment, the pH of the post-wash buffer is between about 4.8 and about 5.1. In yet another preferred embodiment, the pH of the post-wash buffer is between about 4.9 and about 5.0.

As compared to methods previously employed for the clarification of the suspension formed from the second precipitation step, the present invention provides, in several embodiments, methods that result in improved IgG yields and purity in the clarified Fraction II+III suspension. In one aspect, the improvement relates to a method in which a reduced amount of IgG is lost in the Modified Fraction II+III filter cake. In other aspect, the improvement relates to a method in which a reduced amount of an impurity is found in the clarified Fraction II+III suspension.

In one embodiment, the process improvements are realized by inclusion of a fumed silica treatment prior to filtration or centrifugal clarification of a Fraction II+III suspension. In certain embodiments, the fumed silica treatment will include addition of from about 0.01 kg/kg II+III paste to about 0.07 kg/kg II+III paste, or from about 0.02 kg/kg II+III paste to about 0.06 kg/kg II+III paste, or from about 0.03 kg/kg II+III paste to about 0.05 kg/kg II+III paste, or about 0.02 kg/kg II+III paste, 0.03 kg/kg II+III paste, 0.04 kg/kg II+III paste, 0.05 kg/kg II+III paste, 0.06 kg/kg II+III paste, 0.07 kg/kg II+III paste, 0.08 kg/kg II+III paste, 0.09 kg/kg II+III paste, or 0.1 kg/kg II+III paste, and the mixture will be incubated for between about 50 minutes and about 70 minutes, or about 30, 35, 40, 45, 50, 55, 60, 65, 70, 75, 80, or more minutes at a temperature between about 2° C. and about 8° C. In another embodiment, the process improvements are realized by inclusion of a fumed silica treatment which reduced the levels of residual fibrinogen, amidolytic activity, and/or prekallikrein activator activity. In a specific embodiment, the process improvements are realized by inclusion of a fumed silica treatment, which reduces the levels of FXI, FXIa, FXII, and FXIIa in the immunoglobulin preparation.

In another embodiment, the process improvements are realized by washing the depth filter with from about 3 to about 5 volumes of the filter dead volume after completing the Modified Fraction II+III suspension filtration step. In certain embodiments, the filter is washed with from about 3.5 volumes and about 4.5 volumes, or at least about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 volumes of the filter dead volume. In a particular embodiment, the filter press is washed with at least about 3.6 dead volumes of suspension buffer.

7. Detergent Treatment

In order to remove additional contaminants from the Modified Fraction II+III filtrate, the sample is next subjected to a detergent treatment. Methods for the detergent treatment of plasma derived fractions are well known in the art. Generally, any standard non-ionic detergent treatment may be used in conjunction with the methods provided herein. For example, an exemplary protocol for a detergent treatment is provided below.

Briefly, in an exemplary embodiment, a detergent, e.g., polysorbate-80, is added to the Modified Fraction II+III filtrate at a final concentration of about 0.2% (w/v) with stirring and the sample is incubated for at least about 30 minutes at a temperature from about 2° C. to about 8° C. Sodium citrate dehydrate is then mixed into the solution at a final concentration of about 8 g/L and the sample is incubated for an additional 30 minutes, with continuous of stirring at a temperature between about 2 to 8° C.

In certain embodiments, any suitable non-ionic detergent is used. Examples of suitable non-ionic detergents include, without limitation, Octylglucoside, Digitonin, C12E8, Lubrol, Triton X-100, Nonidet P-40, Tween-20 (i.e., polysorbate-20), Tween-80 (i.e., polysorbate-80), an alkyl poly (ethylene oxide), a Brij detergent, an alkylphenol poly (ethylene oxide), a poloxamer, octyl glucoside, decyl maltoside, and the like.

In one embodiment, a process improvement is realized by adding the detergent reagents (e.g., polysorbate-80 and sodium citrate dehydrate) by spraying rather than by fluent addition. In other embodiments, the detergent reagents may be added as solids to the Modified Fraction II+III filtrate while the sample is being mixed to ensure rapid distribution of the additives. In certain embodiments, it is preferable to add solid reagents by sprinkling the solids over a delocalized surface area of the filtrate such that local overconcentration does not occur, such as in fluent addition.

8. Third Precipitation Event—Precipitation G

In exemplary embodiments, in order to remove several residual small proteins, e.g., albumin and transferrin, a third precipitation is performed at a concentration of 25% alcohol. Briefly, the pH of the detergent treated II+III filtrate is adjusted to from about 6.8 to about 7.2, e.g., from about 6.9 to about 7.1, e.g., about 7.0 with a suitable pH modifying solution (e.g., 1M sodium hydroxide or 1M acetic acid). Cold alcohol is then added to the solution to a final concentration of about 25% (v/v) and the mixture is incubated while stirring at from about −6° C. to about −10° C. for at least 1 hour to form a third precipitate (i.e., precipitate G). In one embodiment, the mixture is incubated for at least 2 hours, or at least 3, 4, 5, 6, 7, 8, 9, 10, 11, 12, 13, 14, 15, 16, 17, 18, 19, 20, 21, 22, 23, 24, or more hours. In a preferred embodiment, the mixture is incubated for at least 2 hours. In an exemplary embodiment, the mixture is incubated for at least 4 hours. In some embodiments, the mixture is incubated for at least 8 hours.

In one embodiment, a process improvement of the invention relates to a method in which a reduced amount of IgG is lost in the supernatant fraction of the third precipitation step. In certain embodiments, the process improvement is realized by adjusting the pH of the solution to from about 6.8 to about 7.2 immediately after or during the addition of the precipitating alcohol. In another embodiment, the process improvement is realized by maintaining the pH of the solution to from about 6.8 to about 7.2 continuously during the precipitation incubation period. In some embodiments, the pH of the solution is adjusted to from about 6.9 to about 7.1 immediately after or during the addition of the precipitating alcohol, or to a pH of about 6.8, 6.9, 7.0, 7.1, or 7.2 immediately after or during the addition of the precipitating alcohol. In a particular embodiment, the pH of the solution is adjusted to about 7.0 immediately after or during the addition of the precipitating alcohol. In certain embodiments, the pH of the solution is maintained at from about 6.9 to about 7.1 continuously during the precipitation incubation period, or at a pH of about 7.0 continuously during the precipitation incubation period. According to the improved method, in certain embodiments, a reduced amount of IgG is lost in the supernatant fraction of the third precipitation step as compared to an analogous precipitation step in which the pH of the solution is adjusted prior to but not after addition of the precipitating alcohol or to an analogous precipitation step in which the pH of the solution is not maintained during the entirety of the precipitation incubation period. In one embodiment, the pH is maintained at the desired pH during the precipitation hold or incubation time by continuously adjusting the pH of the solution. In one embodiment, the alcohol is ethanol.

In some embodiments, the process improvement is realized by adding the precipitating alcohol and/or the solution used to adjust the pH by spraying, rather than by bulk, fluent addition. As such, in certain embodiments, a reduced amount of IgG is lost in the supernatant fraction of the third precipitation step as compared to an analogous precipitation step in which the alcohol and/or solution used to adjust the pH is introduced by fluent addition. In one embodiment, the alcohol is ethanol.

9. Suspension and Filtration of Precipitate G (PptG)

In order to solubilize the IgG content of the precipitate G, a cold extraction buffer is used to re-suspend the PptG. Briefly, the Precipitate G is dissolved 1 to 3.5 in Water for Injection (WFI) at from about 0° C. to about 8° C. to achieve an $AU_{280-320}$ value of from about 40 to 95. The final pH of the solution, which is stirred for at least 2 hours, is then adjusted to about 5.2±0.2. In one embodiment, this pH adjustment is performed with 1M acetic acid. To increase the solubility of IgG, the conductivity of the suspension is increased to from about 2.5 and about 6.0 mS/cm. In one embodiment, the conductivity is increased by the addition of sodium chloride. The suspended PptG solution is then filtered with a suitable depth filter having a nominal pore size of from about 0.1 μm and about 0.4 μm in order to remove any undissolved particles. In one embodiment, the nominal pore size of the depth filter is about 0.2 μm (e.g., Cuno VR06 filter or equivalent) to obtain a clarified filtrate. In another embodiment, the suspended PptG solution is centrifuged to recover a clarified supernatant. Post-wash of the filter is performed using a sodium chloride solution with a conductivity of between about 2.5 and about 6.0 mS/cm. Typically, suitable solutions for the extraction of precipitate G include, WFI and low conductivity buffers. In one embodiment, a low conductivity buffer has a conductivity of less than about 10 mS/cm. In a preferred embodiment, the low conductivity buffer has a conductivity of less than about 9, 8, 7, 6, 5, 4, 3, 2, or 1 mS/cm. In a preferred embodiment, the low conductivity buffer has a conductivity of less than about 6 mS/cm. In another preferred embodiment, the low conductivity buffer has a conductivity of less than about 4 mS/cm. In another preferred embodiment, the low conductivity buffer has a conductivity of less than about 2 mS/cm.

10. Solvent Detergent Treatment

In order to inactivate various viral contaminants which may be present in plasma-derived products, the clarified PptG filtrate is next subjected to a solvent detergent (S/D) treatment. Methods for the detergent treatment of plasma derived fractions are well known in the art (for review see, Pelletier J P et al., *Best Pract Res Clin Haematol.* 2006; 19(1):205-42). Generally, any standard S/D treatment may be used in conjunction with the methods provided herein. An exemplary protocol for an S/D treatment is provided below.

Briefly, Triton X-100, Tween-20, and tri(n-butyl)phosphate (TNBP) are added to the clarified PptG filtrate at final concentrations of about 1.0%, 0.3%, and 0.3%, respectively. The mixture is then stirred at a temperature between about 18° C. and about 25° C. for at least about an hour.

In one embodiment, a process improvement is realized by adding the S/D reagents (e.g., Triton X-100, Tween-20, and TNBP) by spraying rather than by bulk, fluent addition. In other embodiments, the detergent reagents may be added as solids to the clarified PptG filtrate, which is being mixed to ensure rapid distribution of the S/D components. In certain embodiments, it is preferable to add solid reagents by sprinkling the solids over a delocalized surface area of the filtrate such that local overconcentration does not occur, such as in fluent addition.

11. Ion Exchange Chromatography

In order to further purify and concentrate IgG from the S/D treated PptG filtrate, cation exchange and/or anion exchange chromatography can be employed. Methods for purifying and concentrating IgG using ion exchange chromatography are well known in the art. For example, U.S. Pat. No. 5,886,154 describes a method in which a Fraction II+III precipitate is extracted at low pH (between about 3.8 and 4.5), followed by precipitation of IgG using caprylic acid, and finally implementation of two anion exchange chromatography steps. U.S. Pat. No. 6,069,236 describes a chromatographic IgG purification scheme that does not rely on alcohol precipitation at all. PCT Publication No. WO 2005/073252 describes an IgG purification method involving the extraction of a Fraction II+III precipitate, caprylic acid treatment, PEG treatment, and a single anion exchange chromatography step. U.S. Pat. No. 7,186,410 describes an IgG purification method involving the extraction of either a Fraction I+II+III or a Fraction II precipitate followed by a single anion exchange step performed at an alkaline pH. U.S. Pat. No. 7,553,938 describes a method involving the extraction of either a Fraction I+II+III or a Fraction II+III precipitate, caprylate treatment, and either one or two anion exchange chromatography steps. U.S. Pat. No. 6,093,324 describes a purification method comprising the use of a macroporous anion exchange resin operated at a pH between about 6.0 and about 6.6. U.S. Pat. No. 6,835,379 describes a purification method that relies on cation exchange chromatography in the absence of alcohol fractionation. The disclosures of the above publications are hereby incorporated by reference in their entireties for all purposes.

In one embodiment of the methods of the present invention, the S/D treated PptG filtrate may be subjected to both cation exchange chromatography and anion exchange chromatography. For example, in one embodiment, the S/D treated PptG filtrate is passed through a cation exchange column, which binds the IgG in the solution. The S/D reagents can then be washed away from the absorbed IgG, which is subsequently eluted off of the column with a high pH elution buffer having a pH between about 8.0 and 9.0. In this fashion, the cation exchange chromatography step can be used to remove the S/D reagents from the preparation, concentrate the IgG containing solution, or both. In certain embodiments, the pH elution buffer may have a pH from about 8.2 and about 8.8, or from about 8.4 and about 8.6, or a pH of about 8.0, 8.1, 8.2, 8.3, 8.4, 8.5, 8.6, 8.7, 8.8, 8.9, or 9.0. In a preferred embodiment, the pH of the elution buffer is about 8.5±0.1.

In certain embodiments, the eluate from the cation exchange column may be adjusted to a lower pH, for example from about 5.5 to about 6.5, and diluted with an appropriate buffer such that the conductivity of the solution is reduced. In certain embodiments, the pH of the cation exchange eluate may be adjusted to a pH between about 5.7 and about 6.3, or between about 5.9 and about 6.1, or a pH of about 5.5, 5.6, 5.7, 5.8, 5.9, 6.0, 6.1, 6.2, 6.3, 6.4, or 6.5. In a preferred embodiment, the pH of the eluate is adjusted to a pH of about 6.0±0.1. The eluate is then loaded onto an anion exchange column, which binds several contaminants found in the preparation. The column flow through, containing the IgG fraction, is collected during column loading and washing. In certain embodiments, the ion exchange chromatographic steps of the present invention can be performed in column mode, batch mode, or in a combination of the two.

In certain embodiments, a process improvement is realized by adding the solution used to adjust the pH by spraying, rather than by bulk, fluent addition.

12. Nanofiltration and Ultra/Diafiltration

In order to further reduce the viral load of the IgG composition provided herein, the anion exchange column effluent, in some embodiments, is nanofiltered using a suitable nanofiltration device. In certain embodiments, the nanofiltration device has a mean pore size of from about 15 nm to about 200 nm. Examples of nanofilters suitable for this use include, without limitation, DVD, DV 50, DV 20 (Pall), Viresolve NFP, Viresolve NFR (Millipore), Planova 15N, 20N, 35N, and 75N (Planova). In a specific embodiment, the nanofilter may have a mean pore size of between about 15 nm and about 72 nm, or between about 19 nm and about 35 nm, or of about 15 nm, 19 nm, 35 nm, or 72 nm. In a preferred embodiment, the nanofilter will have a mean pore size of about 35 nm, such as an Asahi PLANOVA 35N filter or equivalent thereof.

Optionally, ultrafiltration/diafiltration may performed to further concentrate the nanofiltrate. In one embodiment, an open channel membrane is used with a specifically designed post-wash and formulation near the end the production process render the resulting IgG compositions about twice as high in protein concentration (200 mg/mL) compared to state of the art IVIGs (e.g., GAMMAGARD® LIQUID) without affecting yield and storage stability. With most of the commercial available ultrafiltration membranes a concentration of 200 mg/mL IgG cannot be reached without major protein losses. These membranes will be blocked early and therefore adequate post-wash is difficult to achieve. Therefore open channel membrane configurations have to be used. Even with open channel membranes, a specifically designed post-wash procedure has to be used to obtain the required concentration without significant protein loss (less than 2% loss). Even more surprising is the fact that the higher protein concentration of 200 mg/mL does not diminsh the virus inactivation capacity of the low pH storage step.

Subsequent to nanofiltration, the filtrate may be further concentrated by ultrafiltration/diafiltration. In one embodiment, the nanofiltrate is concentrated by ultrafiltration to a protein concentration of from about 2% to about 10% (w/v). In certain embodiments, the ultrafiltration is carried out in a cassette with an open channel screen and the ultrafiltration membrane has a nominal molecular weight cut off (NMWCO) of less than about 100 kDa or less than about 90, 80, 70, 60, 50, 40, 30, or fewer kDa. In a preferred embodiment, the ultrafiltration membrane has a NMWCO of no more than 50 kDa.

Upon completion of the ultrafiltration step, the concentrate may further be concentrated via diafiltration against a solution suitable for intravenous or intramuscular administration. In certain embodiments, the diafiltration solution may comprise a stabilizing and/or buffering agent. In a preferred embodiment, the stabilizing and buffering agent is glycine at an appropriate concentration, for example between about 0.20 M and about 0.30M, or between about 0.22M and about 0.28M, or between about 0.24M and about 0.26 mM, or at a concentration of about 2.0, 2.1, 2.2, 2.3, 2.4, 2.5, 2.6, 2.7, 2.8, 2.9, or 3.0. In a preferred embodiment, the diafiltration buffer contains at or about 0.25 M glycine.

Typically, the minimum exchange volume is at least about 3 times the original concentrate volume or at least about 4, 5, 6, 7, 8, 9, or more times the original concentrate volume. The IgG solution may be concentrated to a final protein concentration of from about 5% to about 25% (w/v), or from about 6% to about 18% (w/v), or from about 7% to about 16% (w/v), or from about 8% to about 14% (w/v), or from about 9% to about 12%, or to a final concentration of about 5%, or 6%, 7%, 8%, 9%, 10%, 11%, 12%, 13%, 14%, 15%, 16%, 17%, 18%, 19%, 20%, 21%, 22%, 23%, 24%, 25% or higher. In one embodiment, a final protein concentration of at least about 23% is achieved without adding the post-wash fraction to the concentrated solution. In another embodiment, a final protein concentration of at least about 24% is achieved without adding the post-wash fraction to the concentrated solution a final protein concentration of at least about 25% is achieved without adding the post-wash fraction to the concentrated solution. Typically, at the end of the concentration process, the pH of the solution will be between about 4.6 to 5.1.

In an exemplary embodiment, the pH of the IgG composition is adjusted to about 4.5 prior to ultrafiltration. The solution is concentrated to a protein concentration of 5±2% w/v through ultrafiltration. The UF membrane has a nominal molecular weight cut off (NMWCO) of 50,000 Daltons or less (Millipore Pellicon Polyether sulfon membrane). The concentrate is diafiltered against ten volumes of 0.25 M glycine solution, pH 4.5±0.2. Throughout the ultra-diafiltration operation the solution is maintained at a temperature of between about 2° C. to about 8° C. After diafiltration, the solution is concentrated to a protein concentration of at least 11% (w/v).

13. Formulation

Upon completion of the diafiltration step, the protein concentration of the solution is adjusted to with the diafiltration buffer to a final concentration of from about 5% to about 20% (w/v), or from about 6% to about 18% (w/v), or from about 7% to about 16% (w/v), or from about 8% to about 14% (w/v), or from about 9% to about 12%, or to a final concentration of about 5%, or 6%, 7%, 8%, 9%, 10%, 11%, 12%, 13%, 14%, 15%, 16%, 17%, 18%, 19%, or 20%. In an exemplary embodiment, the final protein concentration of the solution is from about 9% to about 11%, e.g., 10%.

In various embodiments, the formulated bulk solution is further sterilized by filtering through a membrane filter with an absolute pore size of no more than about 0.22 micron, for example about 0.2 micron. The solution is optionally aseptically dispensed into final containers for proper sealing, with samples taken for testing.

In one embodiment, the IgG composition is further adjusted to a concentration of about 10.2±0.2% (w/v) with diafiltration buffer. The pH is adjusted to about 4.4 to about 4.9 if necessary. Finally, the solution is sterile filtered and incubated for three weeks at about 30° C.

14. Methods of Treatment

As routinely practiced in modern medicine, sterilized preparations of concentrated immunoglobulins (especially IgGs) are used for treating medical conditions that fall into these three main classes: immune deficiencies, inflammatory and autoimmune diseases, and acute infections. These IgG preparations may also be useful for treating multiple sclerosis (especially relapsing-remitting multiple sclerosis or RRMS), Alzheimer's disease, and Parkinson's disease. The purified IgG preparation of this invention is suitable for these purposes, as well as other clinically accepted uses of IgG preparations.

The FDA has approved the use of IVIG to treat various indications, including allogeneic bone marrow transplant, chronic lymphocytic leukemia, idiopathic thrombocytopenic purpura (ITP), pediatric HIV, primary immunodeficiencies, Kawasaki disease, chronic inflammatory demyelinating polyneuropathy (CIDP), and kidney transplant with a high antibody recipient or with an ABO incompatible donor. In certain embodiments, the IVIG compositions provided herein are useful for the treatment or management of these diseases and conditions.

Furthermore, off-label uses for IVIG are commonly provided to patients for the treatment or management of various indications, for example, chronic fatigue syndrome, Clostridium difficile colitis, dermatomyositis and polymyositis, Graves' ophthalmopathy, Guillain-Barré syndrome, muscular dystrophy, inclusion body myositis, Lambert-Eaton syndrome, Lupus erythematosus, multifocal motor neuropathy, multiple sclerosis (MS), myasthenia gravis, neonatal alloimmune thrombocytopenia, Parvovirus B19 infection, pemphigus, post-transfusion purpura, renal transplant rejection, spontaneous Abortion/Miscarriage, stiff person syndrome, opsoclonus Myoclonus, severe sepsis and septic shock in critically ill adults, toxic epidermal necrolysis, chronic lymphocytic leukemia, multiple myeloma, X-linked agammaglobulinemia, and hypogammaglobulinemia. In certain embodiments, the IVIG compositions provided herein are useful for the treatment or management of these diseases and conditions.

Finally, experimental use of IVIG for the treatment or management of diseases including primary immune deficiency, RRMS, Alzheimer's disease, and Parkinson's disease has been proposed (U.S. Patent Application Publication No. U.S. 2009/0148463, which is herein incorporated by reference in its entirety for all purposes). In certain embodiments, the IVIG compositions provided herein are useful for the treatment or management of primary immune deficiency, RRMS, Alzheimer's disease, or Parkinson's disease. In certain embodiments comprising daily administration, an effective amount to be administered to the subject can be determined by a physician with consideration of individual differences in age, weight, disease severity, route of administration (e.g., intravenous v. subcutaneous) and response to the therapy. In certain embodiments, an immunoglobulin preparation of this invention can be administered to a subject at about 5 mg/kilogram to about 2000 mg/kilogram each day. In additional embodiments, the immunoglobulin preparation can be administered in amounts of at least about 10 mg/kilogram, at last 15 mg/kilogram, at least 20 mg/kilogram, at least 25 mg/kilogram, at least 30 mg/kilogram, or at least 50 mg/kilogram. In additional embodiments, the immunoglobulin preparation can be administered to a subject at doses up to about 100 mg/kilogram, to about 150 mg/kilogram, to about 200 mg/kilogram, to about 250 mg/kilogram, to about 300 mg/kilogram, to about 400 mg/kilogram each day. In other embodiments, the doses of the immunoglobulin preparation can be greater or less. Further, the immunoglobulin preparations can be administered in one or more doses per day. Clinicians familiar with the diseases treated by IgG preparations can determine the appropriate dose for a patient according to criteria known in the art.

In accordance with the present invention, the time needed to complete a course of the treatment can be determined by a physician and may range from as short as one day to more than a month. In certain embodiments, a course of treatment can be from 1 to 6 months.

An effective amount of an IVIG preparation is administered to the subject by intravenous means. The term "effective amount" refers to an amount of an IVIG preparation that results in an improvement or remediation of disease or condition in the subject. An effective amount to be administered to the subject can be determined by a physician with consideration of individual differences in age, weight, the disease or condition being treated, disease severity and response to the therapy. In certain embodiments, an IVIG preparation can be administered to a subject at dose of about 5 mg/kilogram to about 2000 mg/kilogram per administration. In certain embodiments, the dose may be at least about 5 mg/kg, or at least about 10 mg/kg, or at least about 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, or at least about 2000 mg/kg.

The dosage and frequency of IVIG treatment will depend upon, among other factors. the disease or condition being treated and the severity of the disease or condition in the patient. Generally, for primary immune dysfunction a dose of between about 100 mg/kg and about 400 mg/kg body weight will be administered about every 3 to 4 weeks. For neurological and autoimmune diseases, up to 2 g/kg body weight is implemented for three to six months over a five day course once a month. This is generally supplemented with maintenance therapy comprising the administration of between about 100 mg/kg and about 400 mg/kg body weight about once every 3 to 4 weeks. Generally, a patient will receive a dose or treatment about once every 14 to 35 days, or about every 21 to 28 days. The frequency of treatment will depend upon, among other factors, the disease or condition being treated and the severity of the disease or condition in the patient.

In a preferred embodiment, a method of treating an immunodeficiency, autoimmune disease, or acute infection in a human in need thereof is provided, the method comprising administering a pharmaceutical IVIG composition of the present invention. In a related embodiment, the present invention provides IVIG compositions manufactured according to a method provided herein for the treatment of an immunodeficiency, autoimmune disease, or acute infection in a human in need thereof.

In certain embodiments, the immunodeficiency, autoimmune disease, or acute infection is selected from allogeneic bone marrow transplant, chronic lymphocytic leukemia, idiopathic thrombocytopenic purpura (ITP), pediatric HIV, primary immunodeficiencies, Kawasaki disease, chronic inflammatory demyelinating polyneuropathy (CIDP), kidney transplant with a high antibody recipient or with an ABO incompatible donor, chronic fatigue syndrome, Clostridium difficile colitis, dermatomyositis and polymyositis, Graves' ophthalmopathy, Guillain-Barré syndrome, muscular dystrophy, inclusion body myositis, Lambert-Eaton syndrome, Lupus erythematosus, multifocal motor neuropathy, multiple sclerosis (MS), myasthenia gravis, neonatal alloimmune thrombocytopenia, Parvovirus B19 infection, pemphigus, post-transfusion purpura, renal transplant rejection, spontaneous Abortion/Miscarriage, stiff person syndrome, opsoclonus Myoclonus, severe sepsis and septic shock in critically ill adults, toxic epidermal necrolysis, chronic lymphocytic leukemia, multiple myeloma, X-linked agammaglobulinemia, hypogammaglobulinemia, primary immune deficiency, RRMS, Alzheimer's disease, and Parkinson's disease.

15. Pharmaceutical Compositions

In another aspect, the present invention provides pharmaceutical compositions and formulations comprising purified IgG prepared by the methods provided herein. Generally, the IgG pharmaceutical compositions and formulations prepared by the novel methods described herein will have high IgG content and purity. For example, IgG pharmaceutical compositions and formulations provided herein may have a protein concentration of at least about 7% (w/v) and an IgG content of greater than about 95% purity. These high purity IgG pharmaceutical compositions and formulations are suitable for therapeutic administration, e.g., for IVIG therapy. In a preferred embodiment, a pharmaceutical IgG composition is formulated for intravenous administration (e.g., IVIG therapy).

In one embodiment, the pharmaceutical compositions provided herein are prepared by formulating an aqueous IgG composition isolated using a method provided herein. Generally, the formulated composition will have been subjected to at least one, preferably at least two, most preferably at least three, viral inactivation or removal steps. Non-limiting examples of viral inactivation or removal steps that may be employed with the methods provided herein include, solvent detergent treatment (Horowitz et al., *Blood Coagul Fibrinolysis* 1994 (5 Suppl 3):S21-S28 and Kreil et al., *Transfusion* 2003 (43):1023-1028, both of which are herein expressly incorporated by reference in their entirety for all purposes), nanofiltration (Hamamoto et al., *Vox Sang* 1989 (56)230-236 and Yuasa et al., *J Gen Virol.* 1991 (72 (pt 8)): 2021-2024, both of which are herein expressly incorporated by reference in their entirety for all purposes), and low pH incubation at high temperatures (Kempf et al., *Transfusion* 1991 (31)423-427 and Louie et al., *Biologicals* 1994 (22):13-19).

In certain embodiments, pharmaceutical formulations are provided having an IgG content of from about 80 g/L IgG to about 220 g/L IgG. Generally, these IVIG formulations are prepared by isolating an IgG composition from plasma using a method described herein, concentrating the composition, and formulating the concentrated composition in a solution suitable for intravenous administration. The IgG compositions may be concentrated using any suitable method known to one of skill in the art. In one embodiment, the composition is concentrated by ultrafiltration/diafiltration. In some embodiments, the ultrafiltration device used to concentrate the composition will employ an ultrafiltration membrane having a nominal molecular weight cut off (NMWCO) of less than about 100 kDa or less than about 90, 80, 70, 60, 50, 40, 30, or fewer kDa. In a preferred embodiment, the ultrafiltration membrane has a NMWCO of no more than 50 kDa. Buffer exchange may be achieved using any suitable technique known to one of skill in the art. In a specific embodiment, buffer exchange is achieved by diafiltration.

In one specific embodiment, a pharmaceutical composition of IgG is provided, wherein the IgG composition was purified from a C1-INH depleted supernatant fraction comprising IgG, the method comprising:

(a) contacting the C1-INH depleted supernatant fraction with heparin, thereby forming a heparinized fraction; and (b) isolating IgG from the heparinized fraction, thereby forming an IgG enriched fraction.

In a specific embodiment, a pharmaceutical composition of IgG is provided, wherein the IgG composition was purified from heparinized fraction using a method comprising the steps of (a) precipitating the heparinized fraction, in a first precipitation step, with from about 6% to about 10% ethanol at a pH of from about 7.0 to 7.5 to obtain a first precipitate and a first supernatant; (b) adjusting the ethanol concentration of the heparinized fraction of step (a) to about 25% (v/v) at a temperature from about −5° C. to about −9° C., thereby forming a mixture, (c) separating liquid and precipitate from the mixture of step (b), (d) re-suspending the precipitate of step (c) with a buffer containing phosphate and acetate, wherein the pH of the buffer is adjusted with 600 ml of glacial acetic acid per 1000 L of buffer, thereby forming a suspension, (e) mixing finely divided silicon dioxide ($SiO_2$) with the suspension from step (d) for at least about 30 minutes, (f) filtering the suspension with a filter press, thereby forming a filtrate, (g) washing the filter press with at least 3 filter press dead volumes of a buffer containing phosphate and acetate, wherein the pH of the buffer is adjusted with 150 ml of glacial acetic acid per 1000 L of buffer, thereby forming a wash solution, (h) combining the filtrate of step (f) with the wash solution of step (g), thereby forming a solution, and treating the solution with a detergent, (i) adjusting the pH of the solution of step (h) to about 7.0 and adding ethanol to a final concentration of about 25%, thereby forming a precipitate, (j) separating liquid and precipitate from the mixture of step (i), (k) dissolving the precipitate in an aqueous solution comprising a solvent or detergent and maintaining the solution for at least 60 minutes, (l) passing the solution after step (k) through a cation exchange chromatography column and eluting proteins absorbed on the column in an eluate, (m) passing the eluate from step (l) through an anion exchange chromatography column to generate an effluent, (n) passing the effluent from step (m) through a nanofilter to generate a nanofiltrate, (o) passing the nanofiltrate from step (n) through an ultrafiltration membrane to generate an ultrafiltrate, and (p) diafiltrating the ultrafiltrate from step (o) against a diafiltration buffer to generate a diafiltrate having a protein concentration from about 8% (w/v) to about 12% (w/v), thereby obtaining a composition of concentrated IgG.

In certain embodiments, a pharmaceutical composition of IgG is provided, wherein the IgG composition is prepared using a method provided herein that comprises improvements in two or more of the fractionation process steps described above. For example, in certain embodiments the improvements may be found in the first precipitation step, the Modified Fraction II+III precipitation step, the Modified Fraction II+III dissolution step, and/or the Modified Fraction II+III suspension filtration step.

In certain embodiments, a pharmaceutical composition of IgG is provided, wherein the IgG composition is prepared using a purification method described herein, wherein the method comprises the spray addition of one or more solutions that would otherwise be introduced into a plasma fraction by fluent addition. For example, in certain embodiments the method will comprise the introduction of alcohol (e.g., ethanol) into a plasma fraction by spraying. In other embodiments, solutions that may be added to a plasma fraction by spraying include, without limitation, a pH modifying solution, a solvent solution, a detergent solution, a dilution buffer, a conductivity modifying solution, and the like. In a preferred embodiment, one or more alcohol precipitation steps is performed by the addition of alcohol to a plasma fraction by spraying. In a second preferred embodiment, one or more pH adjustment steps is performed by the addition of a pH modifying solution to a plasma fraction by spraying.

In certain embodiments, a pharmaceutical composition of IgG is provided, wherein the IgG composition is prepared by a purification method described herein, wherein the method comprises adjusting the pH of a plasma fraction being precipitated after and/or concomitant with the addition of the precipitating agent (e.g., alcohol or polyethelene glycol). In some embodiments, a process improvement is provided in which the pH of a plasma fraction being actively precipitated is maintained throughout the entire precipitation incubation or hold step by continuous monitoring and adjustment of the pH. In preferred embodiments the adjustment of the pH is performed by the spray addition of a pH modifying solution.

In one embodiment, the present invention provides a pharmaceutical composition of IgG comprising a protein concentration of from about 70 g/L to about 130 g/L. In certain embodiments, the protein concentration of the IgG composition is between about 80 g/L and about 120 g/L, e.g., between about 90 g/L and about 110 g/L, e.g., about 100 g/L, or any suitable concentration within these ranges, for example about 70 g/L, 75 g/L, 80 g/L, 85 g/L, 90 g/L, 95 g/L, 100 g/L, 105 g/L, 110 g/L, 115 g/L, 120 g/L, 125 g/L, or 130 g/L. In a preferred embodiment, a pharmaceutical composition is provided having a protein concentration of at or about 100 g/L. In a particularly preferred embodiment, the pharmaceutical composition will have a protein concentration of at or about 102 g/L.

In another embodiment, the present invention provides a pharmaceutical composition of IgG comprising a protein concentration of from about 170 g/L to about 230 g/L. In certain embodiments, the protein concentration of the IgG composition is from about 180 g/L to about 220 g/L, e.g., between about 190 g/L and about 210 g/L, e.g., about 200 g/L, or any suitable concentration within these ranges, for example about 170 g/L, 175 g/L, 180 g/L, 185 g/L, 190 g/L, 195 g/L, 200 g/L, 205 g/L, 210 g/L, 215 g/L, 220 g/L, 225 g/L, or 230 g/L. In a preferred embodiment, a pharmaceutical composition is provided having a protein concentration of at or about 200 g/L.

The methods provided herein allow for the preparation of IgG pharmaceutical compositions having very high levels of purity. For example, in one embodiment, at least about 95% of the total protein in a composition provided herein will be IgG. In other embodiments, at least about 96% of the protein is IgG, or at least about 97%, 98%, 99%, 99.5%, or more of the total protein of the composition will be IgG. In a preferred embodiment, at least 97% of the total protein of the composition will be IgG. In another preferred embodiment, at least 98% of the total protein of the composition will be IgG. In another preferred embodiment, at least 99% of the total protein of the composition will be IgG.

Similarly, the methods provided herein allow for the preparation of IgG pharmaceutical compositions which containing extremely low levels of contaminating agents. For example, in certain embodiments, IgG compositions are provided that contain less than about 100 mg/L IgA. In other embodiments, the IgG composition will contain less than about 50 mg/L IgA, preferably less than about 35 mg/L IgA, most preferably less than about 20 mg/L IgA.

The pharmaceutical compositions provided herein will typically comprise one or more buffering agents or pH stabilizing agents suitable for intravenous, subcutaneous, and/or intramuscular administration. Non-limiting examples of buffering agents suitable for formulating an IgG composition provided herein include glycine, citrate, phosphate, acetate, glutamate, tartrate, benzoate, lactate, histidine or other amino acids, gluconate, malate, succinate, formate, propionate, carbonate, or any combination thereof adjusted to an appropriate pH. Generally, the buffering agent will be sufficient to maintain a suitable pH in the formulation for an extended period of time. In a preferred embodiment, the buffering agent is glycine.

In some embodiments, the concentration of buffering agent in the formulation will be from about 100 mM to about 400 mM, e.g., about 150 mM to about 350 mM, e.g., about 200 mM and about 300 mM, e.g., 250 mM. In a particularly preferred embodiment, the IVIG composition will comprise from about 200 mM to about 300 mM glycine, e.g., about 250 mM glycine.

In certain embodiments, the pH of the formulation will be from about 4.1 to about 5.6, e.g., between about 4.4 and about 5.3, e.g., 4.6 and about 5.1. In particular embodiments, the pH of the formulation may be about 4.1, 4.2, 4.3, 4.4, 4.5, 4.6, 4.7, 4.8, 4.9, 5.0, 5.1, 5.2, 5.3, 5.4, 5.5, or 5.6. In a preferred embodiment, the pH of the formulation will be from about 4.6 to about 5.1.

In some embodiments, the pharmaceutical compositions provided herein may optionally further comprise an agent for adjusting the osmolarity of the composition. Non-limiting examples of osmolarity agents include mannitol, sorbitol, glycerol, sucrose, glucose, dextrose, levulose, fructose, lactose, polyethylene glycols, phosphates, sodium chloride, potassium chloride, calcium chloride, calcium gluconoglucoheptonate, dimethyl sulfone, and the like.

Typically, the formulations provided herein will have osmolarities that are comparable to physiologic osmolarity, about 285 to 295 mOsmol/kg (Lacy et al., *Drug Information Handbook—Lexi-Comp* 1999:1254. In certain embodiments, the osmolarity of the formulation will be between about 200 mOsmol/kg and about 350 mOsmol/kg, preferably between about 240 and about 300 mOsmol/kg. In particular embodiments, the osmolarity of the formulation will be about 200 mOsmol/kg, or 210 mOsmol/kg, 220 mOsmol/kg, 230 mOsmol/kg, 240 mOsmol/kg, 245 mOsmol/kg, 250 mOsmol/kg, 255 mOsmol/kg, 260 mOsmol/kg, 265 mOsmol/kg, 270 mOsmol/kg, 275 mOsmol/kg, 280 mOsmol/kg, 285 mOsmol/kg, 290 mOsmol/kg, 295 mOsmol/kg, 300 mOsmol/kg, 310 mOsmol/kg, 320 mOsmol/kg, 330 mOsmol/kg, 340 mOsmol/kg, 340 mOsmol/kg, or 350 mOsmol/kg.

The IgG formulations provided herein are generally stable in liquid form for an extended period of time. In certain embodiments, the formulations are stable for at least about 3 months at room temperature, or at least about 4, 5, 6, 7, 8, 9, 10, 11, 12, 13, 14, 15, 16, 17, 18, 19, 20, 21, 22, 23, or 24 months at room temperature. The formulation will also generally be stable 6 or at least about 18 months under refrigerated conditions (typically between about 2° C. and about 8° C.), or for at least about 21, 24, 27, 30, 33, 36, 39, 42, or 45 months under refrigerated conditions.

EXAMPLES

The following examples are provided by way of illustration only and not by way of limitation. Those of skill in the art will readily recognize a variety of non-critical parameters that could be changed or modified to yield essentially the same or similar results.

Abbreviations Used:

CAE, Cellulose Acetate Electrophoresis; CZE, Capillary Zone Electrophoresis; FC, Final Container; NAPTT, Non-Activated Partial Thromboplastin Time; NP, Normal Plasma; PKA, PreKallikrein Activity; PL-1, amidolytic activity measured with chromogenic substrate PL-1; PptG, Precipitate G; TGA, Thrombin Generation Assay; TP, Total Protein

Example 1

The present example demonstrates that significant amounts of fibrinogen, amidolytic activity, prekallikrein activity can be removed from the PptG precipitate obtained from the C1-INH depleted plasma supernatant (DDCPP).

The fibrinogen content from starting material to supernatant I is reduced from 0.94 to 0.26 g/L DDCPP for variant native (see Table 1), from 1.23 to 0.34 g/L DDCPP for variant heparin (see Table 2) and from 1.4 to 0.37 g/L DDCPP for variant NaCl (see Table 3). Further reduction takes place during aerosol treatment and filtration to 0.01 g/L for the variant heparin (Table 2) and to 0.02 g/L DDCPP for both other variants (Table 1 and Table 3). Fibrinogen in the PptG dissolved samples from the 6 lots is 0.1%-0.3% of total protein (Table 4). The fibrinogen content at this step is equal to the content in the conformance lots produced from PptG (0.1-0.3% of Total Protein). Fibrinogen was below the detection limit at the final container level (see Table 15).

The fractionation II+III separates raw immunoglobulins (II+III precipitate) from raw albumin (II+III supernatant). Haptoglobin and transferrin are mainly kept in the II+III supernatant (see Table 1, Table 2 and Table 3). C3 complement is low at the starting Cohn pool and removed during Aerosil treatment and filtration step from 0.03-0.05 g/L DDCPP to 0.004 g/L DDCPP for the heparin and 0.01 g/L DDCPP for both other variants. FXI protein is reduced from about 1000 U/L DDCPP to 148 U/L DDCPP for the heparin, to 383 U/L DDCPP for native and to 461 U/L DDCPP for the NaCl variant. Aerosil treatment and filtration step reduces fibrinogen, haptoglobin, together with parts of IgA, IgM and FXI protein.

In PptG low content of low molecular weight components as measured by Molecular size distribution (see table 4) are found. Transferrin and α2 macroglobulin remain in the PptG supernatant (Table 1 to Table 3). IgA content (7.7% to 10.9% of Total Protein (TP) measured by ELISA) in PptG dissolved has a slightly lower range as in the conformance lots in VIE (9.6-12.7% of TP). In the PptG dissolved α2-macroglobulin level varies between 4.7 to 5.6% of TP (Table 4). FXI protein is similar high for all lots with variant native and variant NaCl (37.5-41.9 U/g protein) in PptG, but lower for the lots where heparin was added (12.1-12.4 U/g protein) (see Table 4). This is even better reflected by the g/L DDCPP values which are shown in Table 4.

TABLE 1

Upstream intermediate results (Cohn pool till PptG supernatant) -native

| Upstream Variant native | | DDCPP Cohn pool (4/4) | Supernatant I (4/8) | Supernatant II-i-III (5/8) | II-i-III suspension (6/5) | CUNO filtrate (7/13) | PptG supernatant (8/6) |
|---|---|---|---|---|---|---|---|
| Protein (Biuret) | [mg/mL] | 48.23 | 42.66 | 31.03 | 17.54 | 8.52 | 1.07 |
| Molecular size | Aggreagate | 15.07 | | 6.89 | 25.7 | 15.35 | |
| distribution | Oligo/Dimer | 38.52 | | 16.21 | 65.36 | 79.8 | |
| (HPLC) [% area] | Monomer | 46.13 | | 76.71 | 5.82 | 4.64 | |
| | Fragments | 0.24 | | 0.19 | 3.12 | 0.21 | |
| IgA (ELISA) | [mg/mL] | 1.47 | 1.27 | 0.25 | 1.43 | 0.81 | |
| | [g/L DDCPP] | 1.47 | 1.35 | 0.28 | 0.93 | 0.88 | |
| IgM (ELISA) | [mg/mL] | 0.48 | 0.29 | 0.001 | 0.58 | 0.26 | |
| | [g/L DDCPP] | 0.48 | 0.31 | 0.002 | 0.37 | 0.29 | |
| Fibrinogen | [mg/mL] | 0.94 | 0.24 | 0.0002 | 0.48 | 0.02 | |
| | [g/L DDCPP] | 0.94 | 0.26 | 0.0002 | 0.31 | 0.02 | |
| C3 Complement | [mg/mL] | 0.09 | 0.05 | 0.004 | 0.05 | 0.01 | |
| | [g/L DDCPP] | 0.09 | 0.05 | 0.005 | 0.03 | 0.01 | |
| a1-Antitrypsin | [mg/mL] | 1.39 | 1.15 | | 0.01 | 0.01 | |
| | [g/L DDCPP] | 1.39 | 1.21 | | 0.01 | 0.01 | |
| a2-Macro- globulin | [mg/mL] | 1.33 | 1.14 | 0.31 | 1.26 | 0.76 | 0.19 |
| | [g/L DDCPP] | 1.33 | 1.21 | 0.35 | 0.82 | 0.83 | 0.27 |
| Apolipoprotein | [mg/mL] | 1.25 | 1.11 | 0.71 | >0.019 | 0.003 | |
| | [g/L DDCPP] | 1.25 | 1.17 | 0.81 | | 0.003 | |
| Ceruloplasmin | [mg/mL] | 0.02 | | 0.002 | 0.02 | 0.002 | 0.001 |
| | [g/L DDCPP] | 0.02 | | 0.002 | 0.02 | 0.002 | 0.001 |
| FXI protein | [U/mL] | 1.14 | 1.03 | 0.21 | 1.13 | 0.35 | |
| | [U/L DDCPP] | 1140 | 1089 | 241 | 737 | 383 | |
| Haptoglobin | [mg/mL] | 1.06 | | 0.94 | 0.04 | 0.01 | 0.01 |
| | [g/L DDCPP] | 1.06 | | 1.08 | 0.02 | 0.01 | 0.01 |
| Transferrin | [mg/mL] | 2.32 | 2.08 | 1.91 | 0.18 | 0.11 | 0.08 |
| | [g/L DDCPP] | 2.32 | 2.20 | 2.18 | 0.12 | 0.12 | 0.12 |

TABLE 2

Upstream intermediate results (Cohn pool till PptG supernatant) -variant heparin

| Upstream Variant heparin | | Cohn pool (4/4) | Supernatant I (4/8) | Supernatant II + III (5/8) | II + III suspension (6/5) | CUNO filtrate (7/13) | PptG supernatant (8/6) |
|---|---|---|---|---|---|---|---|
| Protein (Biuret) | [mg/mL] | 47.42 | 42.31 | 31.26 | 20.04 | 7.33 | 0.92 |
| Molecular size | Aggreagate | 12.79 | | 10.38 | 22.80 | 15.39 | |
| distribution | Oligo/Dimer | 37.78 | | 13.96 | 69.88 | 79.99 | |
| (HPLC) [% area] | Monomer | 49.19 | | 75.14 | 6.60 | 4.49 | |
| | Fragments | 0.24 | | 0.51 | 0.72 | 0.13 | |
| IgA (ELISA) | [mg/mL] | 1.63 | 1.34 | 0.26 | 1.55 | 0.66 | |
| | [g/L DDCPP] | 1.63 | 1.42 | 0.30 | 1.00 | 0.81 | |
| IgM (ELISA) | [mg/mL] | 0.56 | 0.31 | 0.002 | 0.55 | 0.19 | |
| | [g/L DDCPP] | 0.56 | 0.33 | 0.002 | 0.35 | 0.23 | |
| Fibrinogen | [mg/mL] | 1.23 | 0.32 | 0.0004 | 0.69 | 0.008 | |
| | [g/L DDCPP] | 1.23 | 0.34 | 0.0004 | 0.44 | 0.01 | |
| C3 Complement | [mg/mL] | 0.09 | 0.05 | 0.0003 | 0.05 | 0.003 | |
| | [g/L DDCPP] | 0.09 | 0.05 | 0.0003 | 0.03 | 0.004 | |
| a1-Antitrypsin | [mg/mL] | 1.49 | 1.40 | | 0.04 | 0.007 | |
| | [g/L DDCPP] | 1.49 | 1.49 | | 0.03 | 0.01 | |
| a2-Macro- globulin | [mg/mL] | 1.32 | 1.15 | 0.28 | 1.37 | 0.67 | 0.19 |
| | [g/L DDCPP] | 1.32 | 1.22 | 0.32 | 0.88 | 0.82 | 0.31 |
| Ceruloplasmin | [mg/mL] | 0.03 | | 0.01 | 0.01 | 0.003 | 0.001 |
| | [g/L DDCPP] | 0.03 | | 0.01 | 0.01 | 0.003 | 0.001 |
| FXI protein | [U/mL] | 1.1 | 0.87 | 0.08 | 1.54 | 0.12 | |
| | [U/L DDCPP] | 1100 | 922 | 92 | 994 | 148 | |
| Haptoglobin | [mg/mL] | 1.15 | | 0.91 | 0.04 | 0.006 | 0.004 |
| | [g/L DDCPP] | 1.15 | | 1.04 | 0.03 | 0.01 | 0.01 |
| Transferrin | [mg/mL] | 2.27 | 1.96 | 1.68 | 0.16 | 0.08 | 0.06 |
| | [g/L DDCPP] | 2.27 | 2.07 | 1.93 | 0.10 | 0.10 | 0.10 |

TABLE 3

Upstream intermediate results (Cohn pool till PptG supernatant) -variant NaCl

| Upstream Variant NaCl | | Cohn pool (4/4) | Supernatant I (4/8) | Supernatant II + III (5/8) | II + III suspension (6/5) | CUNO filtrate (7/13) | PptG supernatant (8/6) |
|---|---|---|---|---|---|---|---|
| Protein (Biuret) | [mg/mL] | 48.54 | 43.40 | 30.78 | 12.45 | 7.00 | 0.89 |
| Molecular size | Aggreagate | 13.16 | | 11.13 | 22.22 | 16.99 | |
| distribution | Oligo/Dimer | 38.93 | | 14.49 | 70.79 | 78.57 | |
| (HPLC) [% area] | Monomer | 47.71 | | 74.01 | 6.81 | 4.36 | |
| | Fragments | 0.18 | | 0.38 | 0.17 | 0.10 | |
| IgA (ELISA) | [mg/mL] | 1.521 | 1.56 | 0.23 | 1.30 | 0.62 | |
| | [g/L DDCPP] | 1.52 | 1.70 | 0.27 | 0.95 | 0.87 | |
| IgM (ELISA) | [mg/mL] | 0.50 | 0.46 | 0.002 | 0.72 | 0.25 | |
| | [g/L DDCPP] | 0.50 | 0.50 | 0.002 | 0.53 | 0.34 | |
| Fibrinogen | [mg/mL] | 1.4 | 0.34 | 0.0005 | 0.49 | 0.02 | |
| | [g/L DDCPP] | 1.4 | 0.37 | 0.0006 | 0.36 | 0.02 | |
| C3 Complement | [mg/mL] | 0.09 | 0.08 | 0.0004 | 0.06 | 0.006 | |
| | [g/L DDCPP] | 0.09 | 0.09 | 0.0005 | 0.05 | 0.009 | |
| a1-Antitrypsin | [mg/mL] | 1.29 | 1.14 | | 0.07 | 0.006 | |
| | [g/L DDCPP] | 1.29 | 1.24 | | 0.05 | 0.008 | |
| a2-Macro- globulin | [mg/mL] | 1.40 | 1.19 | 0.25 | 1.19 | 0.59 | 0.18 |
| | [g/L DDCPP] | 1.40 | 1.30 | 0.30 | 0.87 | 0.83 | 0.32 |
| Ceruloplasmin | [mg/mL] | 0.02 | | 0.007 | 0.015 | 0.001 | <0.00032 |
| | [g/L DDCPP] | 0.02 | | 0.008 | 0.01 | 0.002 | n.a. |
| FXI protein | [U/mL] | 0.99 | 0.96 | 0.25 | 1.1 | 0.33 | |
| | [U/L DDCPP] | 990 | 1047 | 295 | 807 | 461 | |
| Haptoglobin | [mg/mL] | 1.02 | | 0.91 | 0.048 | 0.008 | 0.005 |
| | [g/L DDCPP] | 1.02 | | 1.08 | 0.035 | 0.011 | 0.010 |
| Transferrin | [mg/mL] | 2.44 | 2.02 | 1.76 | 0.15 | 0.08 | 0.06 |
| | [g/L DDCPP] | 2.44 | 2.21 | 2.08 | 0.11 | 0.11 | 0.11 |

TABLE 4

Precipitate G characterization

| Precipitate G dissolved Test | Unit | Native 35 mM | Heparin 35 mM | NaCl 35 mM |
|---|---|---|---|---|
| Protein (Biuret) | [mg/mL] | 69.58 | 73.80 | 75.25 |
| Molecular size | Aggreagate | 10.60 | 9.12 | 11.21 |
| distribution | Oligo/Dimer | 13.76 | 13.44 | 12.76 |
| (HPLC) | Monomer | 75.53 | 77.31 | 75.90 |
| [% area] | Fragments | 0.11 | 0.13 | 0.13 |
| IgA (ELISA) | [mg/mL] | 6.22 | 7.46[1)] | 6.06 |
| | [% of TP] | 8.9 | 10.1[1)] | 8.1 |
| | [g/L DDCPP] | 0.79 | 0.78[1)] | 0.66 |
| IgM (ELISA) | [mg/mL] | 1.81 | 1.80 | 2.43 |
| | [% of TP] | 2.6 | 2.4 | 3.2 |
| | [g/L DDCPP] | 0.23 | 0.19 | 0.27 |
| Fibrinogen | [mg/mL] | 0.18 | 0.09 | 0.21 |
| | [% of TP] | 0.25 | 0.12 | 0.27 |
| | [g/L DDCPP] | 0.02 | 0.01 | 0.02 |
| C3 Complement | [mg/mL] | 0.08 | 0.04 | 0.10 |
| | [% of TP] | 0.12 | 0.05 | 0.13 |
| | [g/L DDCPP] | 0.01 | 0.004 | 0.01 |
| a2-Macro-globulin | [mg/mL] | 3.52 | 3.57 | 3.78 |
| | [% of TP] | 5.06 | 4.84 | 5.02 |
| | [g/L DDCPP] | 0.45 | 0.37 | 0.41 |
| FXI protein | [U/mL] | 2.75 | 0.89 | 2.82 |
| | [U/g TP] | 39.52 | 12.06 | 37.47 |
| | [U/L DDCPP] | 349.3 | 92.9 | 308.0 |

PKA at PptG dissolved varies between below the quantification limit up to 9.4 U/mL. In bulk PKA is below the quantification limit (see Table 5) for all process options. Kallikrein like activity is high at PptG dissolved step (490-733 nmol/mL*min) but can be highly reduced by the downstream process: using 35 mM elution buffer for CM Sepharose chromatography levels are below the quantification limit (<10 nmol/mL*min). Non-activated partial thromboplastin time as tested in FXI deficient plasma is not shortened at the PptG dissolved for any option. Amidolytic activity as measured by chromogenic substrate PL-1 is high in PptG dissolved (97.2-163.1 nmol/mL*min) but reduced in most cases to levels below the quantification limit at final bulk level (<10 nmol/mL*min). Thrombin generation was measured at the PptG dissolved level for information only. The test varies, but TGA measured at this step is lower (113.14% and 103.33% of normal plasma) (monitoring limit of 132% NP for FC) for the lot where heparin was added to the DDCPP. At the bulk—sample before low pH incubation—the TGA value is above the monitoring limit for routine final containers of 132% for all samples. TGA value is 185% to 195% of normal plasma for the runs with 35 mM elution buffer regardless of the addition of NaCl, heparin or native. FXIa values are below the quantification limit for the lot produced with the heparin variant at the PptG dissolved. For both other lots values are fairly high (10.3-16.7 ng/g protein) compared to other studies. For all lots FXIa values were detected at the final bulk. Again lowest values were seen if heparin was added to DDCPP.

The high kallikrein like activity at PptG dissolved is reflected also by the amidolytic activity profile. The substrate specifically measures kallikrein, FXIa and FXIIa which is between 570 and 1780 nmol/ml*min. These values are reduced to between 8 and 22 nmol/ml*min at the final bulk (see Table 5).

TABLE 5

PKA, procoagulant impurities and amidolytic activity results in PptG and bulk

| | | | Experiment | | |
|---|---|---|---|---|---|
| CM Sepharose Elution buffer | | | Native 35 mM | Addition of Heparin 35 mM | Addition of NaCl 35 mM |
| PptG dissolved | PKA U/ml | | <4 | 7.5 | <4 |
| | Kallikrein like activity [nmol/mL*min] | | 555 | 733 | 490 |
| | NAPTT [mg] | | >6.6 | >7.4 | >6.6 |
| | Amidolytic activity (PL-1) [nmol/mL*min] | | 143.6 | 163.1 | 97.2 |
| | TGA [% NP] | | 155.85 | 113.14 | 177.01 |
| | FXI protein | [U/ml] | 2.75 | 0.89 | 2.82 |
| | | [U/g protein] | 39.52 | 12.06 | 37.47 |
| | FXIa | [ng/ml] | 0.719 | <0.25 | 0.830 |
| | | [ng/g protein] | 10.33 | n.a. | 11.03 |
| | Amidolytic activity | | 28.40 | 28.30 | 19.50 |
| | profile | | 32.20 | 39.50 | 19.20 |
| | [nmol/mL*min] | | 661 | 927.0 | 341.0 |
| | | | 1242 | 1716 | 574 |
| Bulk | PKA [U/ml] | | <4 | <4 | <4 |
| | Kallikrein like activity [nmol/mL*min] | | <10 | <10 | 11 |
| | Amidolytic activity (PL-1) [nmol/mL*min] | | 2.30 | <10 | <10 |
| | TGA [% NP] | | 195.49 | 186.59 | 184.96 |
| | FXI protein | [U/ml] | 0.42 | 0.10 | 0.34 |
| | | [U/g protein] | 4.10 | 1.02 | 3.34 |
| | FXIa | [ng/ml] | 4.18 | 1.97 | 1.42 |
| | | [ng/g protein] | 40.77 | 20.01 | 13.95 |
| | Amidolytic activity | | <5 | <5 | <5 |
| | profile | | <5 | <5 | <5 |
| | [nmol/mL*min] | | 7.2 | 5.68 | 7.4 |
| | | | 8.22 | 7.63 | 9.29 |

Example 2

The purity in the Cohn pool, in the II+III supernatant (Albumin) and in the intermediate PptG paste is determined by cellulose acetate electrophoresis (see Table 6). According to the current Gammagard Liquid/KIOVIG specifications the intermediate product, Precipitate G must meet the purity specification of ≥86% gamma-globulin as measured with CAE electrophoresis or equivalent. The PptG pastes obtained from DDCPP (plasma after C1-inhibitor adsorption) clearly met the intermediate specification limit of Gammagard Liquid/KIOVIG of >86% (see Table 6). The addition of heparin and sodium chloride increased the purity from 88% to 93%.

Purity is also measured by CZE at the step PptG dissolved and final container. Ppt G has a γ-globulin purity of 92%-93% and final container purity was 100% γ-globulin (see Table 7).

TABLE 6

Purity of Cohn pool, II + III supernatant and PptG as measured by CAE
Cellulose acetate electrophoresis
Unit Spec ≥86%

| Description of experiment | | Native | | Addition of Heparin | | Addition of NaCl | |
|---|---|---|---|---|---|---|---|
| Upstream lot # | | | | | | | |
| Cohn pool (DDCPP) | Albumin | 67.6 | | 68.1 | | 68.5 | |
| | α,β - globulin | 18.9 | | 18.9 | | 18.6 | |
| | γ - globulin | 9.2 | | 12.0 | | 12.9 | |
| | Prealbumin | 0 | | 0 | | 0 | |
| | Fibrinogen | 4.3 | | 0 | | 0 | |
| II + III supernatant | Albumin | 83 | | 81.2 | | 79.7 | |
| | α,β - globulin | 15.1 | | 17.2 | | 18 | |
| | γ - globulin | 1.9 | | 1.6 | | 2.3 | |
| | Prealbumin | 0 | | 0 | | 0 | |
| | Fibrinogen | 0 | | 0 | | 0 | |
| Downstream lot # | | | | | | | |
| PptG dissolved | Albumin | 0.1 | 0.1 | 0.1 | 0.1 | 0.1 | 0.1 |
| | α,β - globulin | 11.7 | 11.2 | 6.5 | 8.9 | 9.7 | 8.6 |
| | γ - globulin | 88.2 | 88.7 | 93.4 | 91.0 | 90.2 | 91.3 |
| | Den. Protein | — | — | — | — | — | — |

TABLE 7

| Purity of PptG dissolved and Final Container (FC) measured by CZE Purity by Cellulose acetate electrophoresis [%] | | | | | | |
|---|---|---|---|---|---|---|
| | Variant | | | | | |
| Downstream lot# | Native | | Addition of Heparin | | Addition of NaCl | |
| PptG dissolved | 92 | n.d. | 93 | 93 | 93 | 93 |
| Final Container | 100 | 100 | 100 | 100 | 100 | 100 |

Example 3

The high IgG recovery and protein yield is determined to confirm that the starting material is suitable to use for the production of IgG. Proteins and IgG yields are given in % and g/L plasma to demonstrate the process efficiency. The high IgG recovery from Cohn pool till bulk reflects very good process efficiency. Recovery from 68% to 75% based on IgG measurement was obtained (see Table 8 to Table 10). Sodium chloride addition to Cohn pool for adjustment of conductivity results in a slightly lower overall recovery compared to the other two options (68% versus more than 70%).

TABLE 8

| Protein and IgG recovery - native using 35 mM CM elution buffer | | | | | | | | | |
|---|---|---|---|---|---|---|---|---|---|
| | Native | | | | | | | | |
| | Weight | | Protein | Protein yield | | | IgG recovery[1)] | | |
| Process step | corr. [kg] | Protein [%] | determination method | [%] | [%] | [g/L plasma] | [%] | Purity | [g/L plasma] |
| Cohn Pool (DDCPP) | 149.0 | 4.82 | Biuret | 100 | | 48.23 | 100 | 14.7 | 7.09 |
| Supernatant I | 157.5 | 4.27 | Biuret | 93.5 | | 45.10 | 89.7 | 14.1 | 6.36 |
| Supernatant II + III | 170.7 | 3.10 | Biuret | 73.7 | | 35.56 | 2.2 | 0.4 | 0.16 |
| Extract II + III | 97.1 | 1.75 | Biuret | 23.7 | | 11.43 | 88.6 | 54.9 | 6.28 |
| Cuno filtrate | 163.0 | 0.85 | Biuret | 19.3 | | 9.32 | 82.1 | 62.4 | 5.82 |
| PptG supernatant | 209.8 | 0.11 | Biuret | 3.1 | | 1.51 | 1.0 | 4.8 | 0.07 |
| PptG dissolved | 3.1 | 6.96 | Biuret | 18.3 | 100 | 8.84 | 100 | 72.6 | 6.41 |
| | | 6.65 | UV | 17.5 | 100 | 8.44 | | | |
| PptG diss. filtrate | 6.1 | 3.45 | Biuret | 18.2 | 99.1 | 8.76 | 100 | 72.6 | 6.41 |
| CM-eluate | 6.6 | 2.77 | Biuret | 15.7 | 85.8 | 7.58 | 92.8 | 78.5 | 5.95 |
| | | 2.54 | UV | 14.4 | 82.2 | 6.94 | | | |
| ANX flow through | 13.2 | 1.02 | UV | 11.6 | 66.2 | 5.59 | 86.9 | 99.7 | 5.58 |
| Nanofiltrate | 16.0 | 0.83 | UV | 11.4 | 65.1 | 5.49 | 79.0 | 92.3 | 5.07 |
| Sterile bulk | 1.21 | 10.25 | UV | 10.7 | 60.9 | 5.14 | 70.8 | 88.4 | 4.54 |

[1)]measured by QC VIE

TABLE 9

| Protein and IgG recovery - variant heparin using 35 mM CM elution buffer | | | | | | | | | |
|---|---|---|---|---|---|---|---|---|---|
| | NG2C134/P00215NG | | | | | | | | |
| | Weight | | Protein | Protein yield | | | IgG recovery[1)] | | |
| Process step | corr. [kg] | Protein [%] | determination method | [%] | [%] | [g/L plasma] | [%] | Purity | [g/L plasma] |
| Cohn Pool | 150.0 | 4.74 | Biuret | 100 | | 47.42 | 100 | 16.2 | 7.67 |
| Supernatant I | 159.0 | 4.23 | Biuret | 94.6 | | 44.86 | 89.8 | 15.4 | 6.89 |
| Supernatant II + III | 172.2 | 3.13 | Biuret | 75.7 | | 35.89 | 2.0 | 0.4 | 0.15 |
| Extract II + III | 96.9 | 2.00 | Biuret | 27.3 | | 12.94 | 85.0 | 50.4 | 6.52 |
| Cuno filtrate | 185.0 | 0.73 | Biuret | 19.1 | | 9.04 | 79.3 | 67.2 | 6.08 |
| PptG supernatant | 238.5 | 0.09 | Biuret | 3.1 | | 1.46 | 0.8 | 4.2 | 0.06 |
| PptG dissolved | 2.8 | 7.38 | Biuret | 16.2 | 100 | 7.70 | 100 | 73.4 | 5.66 |
| | | 6.54 | UV | 14.4 | 100 | 6.82 | | | |
| PptG diss. filtrate | 5.5 | 3.66 | Biuret | 16.1 | 99.2 | 7.64 | | | |
| CM-eluate | 6.4 | 2.65 | Biuret | 13.4 | 82.5 | 6.35 | 66.6 | 59.3 | 3.77 |
| | | 2.55 | UV | 12.9 | 89.8 | 6.13 | | | |
| ANX flow through | 12.5 | 1.04 | UV | 10.4 | 72.4 | 4.94 | 78.5 | 89.9 | 4.44 |
| Nanofiltrate | 15.3 | 0.83 | UV | 10.0 | 69.8 | 4.76 | 71.1 | 84.5 | 4.02 |
| Sterile bulk | 1.1 | 9.84 | UV | 8.8 | 61.4 | 4.19 | 71.9 | 97.1 | 4.07 |

[1)]measured by QC VIE

TABLE 10

| Protein and IgG recovery - variant NaCl using 35 mM CM elution buffer | | | | | | | | | |
|---|---|---|---|---|---|---|---|---|---|
| | Variant NaCl | | | | | | | | |
| | Weight | | Protein | Protein yield | | | IgG recovery[1)2)] | | |
| Process step | corr. [kg] | Protein [%] | determination method | [%] | [%] | [g/L plasma] | [%] | Purity | [g/L plasma] |
| Cohn Pool | 146.4 | 4.85 | Biuret | 100 | | 48.54 | 100 | 15.5 | 7.54[1)] |
| Supernatant I | 159.7 | 4.34 | Biuret | 97.5 | | 47.34 | 98.4 | 15.7 | 7.42[1)] |
| Supernatant II + III | 172.9 | 3.08 | Biuret | 74.9 | | 36.36 | 3.6 | 0.7 | 0.27[1)] |
| Extract II + III | 107.4 | 1.25 | Biuret | 18.8 | | 9.13 | 91 | 75.1 | 6.86[1)] |
| Cuno filtrate | 204.3 | 0.70 | Biuret | 20.1 | | 9.77 | 85.7 | 66.2 | 6.46[1)] |
| PptG supernatant | 262.2 | 0.09 | Biuret | 3.3 | | 1.60 | 0.6 | 2.9 | 0.05[1)] |
| PptG dissolved | 3.02 | 7.53 | Biuret | 6.9 | 100 | 8.22 | 100 | 75.1 | 6.18[1)] |
| | | 6.79 | UV | 15.3 | 100 | 7.42 | | | |
| PptG diss. filtrate | 6.0 | 3.88 | Biuret | 17.4 | 102.8 | 8.44 | 92.9 | 68.5 | 5.78[2)] |
| CM-eluate | 7.2 | 2.75 | Biuret | 14.7 | 86.9 | 7.15 | 83.9 | 73.1 | 5.22[2)] |
| | | 2.17 | UV | 11.6 | 76.0 | 5.64 | | | |
| ANX flow through | 15.3 | 1.04 | UV | 11.8 | 77.3 | 5.74 | 85.7 | 93.0 | 5.34[2)] |
| Nanofiltrate | 18.4 | 0.83 | UV | 11.4 | 74.4 | 5.52 | 85.4 | 96.2 | 5.31[2)] |
| Sterile bulk | 1.3 | 10.19 | UV | 9.8 | 63.9 | 4.74 | 68.5 | 89.2 | 4.23[1)] |

[1)]measured by QC VIE
[2)]measured by PSP/PSTO

Example 4

Final container release parameters were tested according to the Gammagard Liquid/KIOVIG manufacturing method and summarized in Table 11 for the runs with 35 mM elution buffer. Antibody titer results of release parameters are summarized in Table 12 and Table 13.

Example 5

The release tests for anti-A/anti-B hemagglutinins and anti-D antibodies, antibodies against diphtheria (US only), HAV (EU only), HBsAg, measles (US only), parvo B19 (EU only) and polio (US only) were performed for the final container lots (see Table 12-35 mM elution buffer). All antibody tests met the requirements.

TABLE 11

| Results of Final Container specification tests using 35 mM CM Sepharose elution buffer | | | | | | |
|---|---|---|---|---|---|---|
| Parameter | Unit | Spec. | Native | Addition of Heparin | Addition of NaCl | Conformance lots [1] |
| 35 mM Lot # | | | | | | |
| ACA | [%] | US/EU: NMT 50% or 1 $CH_{50}$U/mg protein. | 31 | 30 | 31 | |
| Glycine | [M] | US: 0.21-0.26 EU: 0.20-0.30 | 0.234 | 0.229 | 0.228 | 0.227-0.234 |
| IgA | [p. g/mL] | EU/US <0.14 mg/mL | 42.0 | 41.2 | 32.9 | — |
| | [p. g/mL @ 10% protein] | | 43.2 | 39.4 | 32.7 | 36-53 |
| IgM | [mg/dL] | for US <100 | <4.17 | <4.17 | <4.17 | <1.6 |
| Molecular size distribution | | | | | | |
| IgG Monomer and Dimer | [%] | 2 95% | 99.6 | 99.6 | 99.6 | n.a. |
| IgG Polymer | | <2% | 0.13 | 0.13 | 0.16 | |
| IgG Fragments (US) | | <3% (US only) | 0.28 | 0.25 | 0.27 | |
| Osmolality | [mOsmol/kg] | EU/US: 240-300 | 269 | 265 | 266 | 261-269 |
| Density | [g/cm$^3$] | For info | 1.032 | 1.033 | 1.032 | 1.031-1.033 |
| pH (diluted) | — | EU/US: 4.6 to 5.1. diluted at 1% protein solution with 0.9% NaCl | 4.5 | 4.5 | 4.5 | 4.7-4.8 |
| PKA activity | [IU/mL] | EU: <10 IU/mL US: <10% CBER ref lot 3 | <4 | <4 | <4 | n.a. |
| Kallikrein like activity | [nmol/mL *min] | For information | <10 | <10 | <10 | |
| Protein identity (human protein) | | EU/US: human protein: positive | positive | positive | positive | positive |
| Protein composition: Purity | | 2 98% gamma globulin | 100 | 100 | 100 | n.a. |
| Endotoxins (LAL) | [EU/mL] | <1.0 EU/mL | <0.500 | <0.500 | <0.500 | n.a. |
| Total Protein (UV) | [mg/mL] | EU/US: 9.0 to 11.0 g/100 mL | 97.0 | 104.5 | 100.9 | n.a. |
| TNBP (tri-N-Butyl-Phosphate) | [ppm] | <1.0 ppm | <0.2 | <0.2 | <0.2 | n.a. |
| Triton X-100 (Octoxynol 9) | [ppm] | <1.0 ppm | <0.4 | <0.4 | <0.1 | n.a. |
| TWEEN 80 (Polysorbate 80) | [ppm] | <100 ppm | <26 | <26 | <26 | n.a. |

TABLE 12

| Antibody levels in the FC (IU/g protein calculated on the total protein) - 35 mM elution buffer | | | | | |
|---|---|---|---|---|---|
| Antibody Test | Unit | Specification | Native | Heparin | NaCl |
| Anti D antibodies | Satisfactory | EU/US: Titer is equal to or less than the NIBSC reference preparation 02/228 or equivalent | satisfactory 1:<2 | satisfactory 1:<2 | satisfactory 1:<2 |
| Hemagglutinins (Anti-A/Anti-B)-antibodies | Anti A | 1:32 (US) or 1:64 (EU) dilutions do not show agglutination for solutions containing max. 30 g/L of immunoglobulin | 1:16 | 1:16 | 1:16 |
| | Anti B | | 1:16 | 1:16 | 1:8 |
| Diphtheria antibodies | [IU/mL] | US only: >1.2 U of US Standard Antitoxin/mL | 8.2 | 9.0 | 8.6 |
| | [IU/g protein] | | 77.6 | 91.5 | 84.0 |
| HAV antibodies | [IU/mL] | EU: >3.5 IU/mL | 10.5 | 10.9 | 11.0 |
| | [IU/g protein] | | 99.3 | 110.8 | 107.5 |
| HBsAg antibodies | [mIU/mL] | EU/US: >0.20 IU/mL (EU: 2 IU/g total protein) | 9787 | 14240 | >10000 |
| | [IU/g protein] | | 92.6 | 144.7 | n.a. |
| Measles antibodies | [Quotient] | US only: >0.30 times the antibody level of CBER Reference measles immune globulin | 0.63 | 0.58 | 0.53 |
| Parvo B19 antibodies | [IU/mL] | EU: >50 IU/mL | 418 | 401 | 307 |
| | [IU/g protein] | | 3954 | 4075 | 3000 |
| Poliomyelitis antibodies | Quotient | US only: >0.2 times the antibody level of CBER Reference polio immune globulin | 0.98 | n.d. | 0.90 |

Example 6

In order to determine the residual serine protease content and activity present in plasma-derived protein compositions, the amidolytic activity profile was determined for the IgG preparations from C1-INH depleted plasma supernatant.

Briefly, the amidolytic activity profile for the plasma-derived protein compositions was determined. PL-1, amidolytic activity profile, TGA, NAPTT, FXIa and FXI protein were tested and results were summarized in Table 13 (35 mM elution buffer). As shown in Table 13, amidolytic activity measured by the chromogenic substrate PL-1 is below the quantification limit for all lots which demonstrates the high reduction potential of the downstream processes regardless the phosphate concentration of the CM elution buffer. The amidolytic activity data generated with different chromogenic substrates show also very low values. NAPTT as tested in FXI deficient plasma is not shortened at the final container samples. FXIa is below the quantification limit using 35 mM CM-elution buffer when heparin was added. The FXI protein test which detects not only FXI but also FXIa has very low values when heparin is added to DDCPP using 35 mM CM elution buffer.

TABLE 13

| Amidolytic activities and procoagulant activities measured at FC using 35 mM elution buffer | | | | |
|---|---|---|---|---|
| Test (SOP#) | Unit | native | Heparin | NaCl |
| Amidolytic activity (PL-1) (KVAACPLM) | [nmol/mL min] | <10 | <10 | <10 |
| Amidolytic activity profile [nmol/mL*min] | S-2222 | <5 | <5 | <5 |
| | S-2251 | <5 | <5 | <5 |
| | S-2288 | <5 | <5 | 5.0 |
| | S-2302 | <5 | <5 | <5 |
| FXI Protein | [U/mL] | 0.33 | 0.08 | 0.25 |
| | [U @ 10% protein] | 0.34 | 0.08 | 0.25 |
| FXIa | [ng/mL] | <0.5 | <0.5 | <0.5 |
| | [ng/g protein] | n.a. | n.a. | n.a. |
| NAPTT | [mg] | >10 | >10 | >10 |
| TGA (LE13A18006) | [% of normal plasma] | 125.21 | 120.45 | 190.11 |

Example 7

FXI protein test is also an indicator throughout the manufacturing process. In Table 14 the overall reduction of FXI protein from DDCPP till the final container are summarized. FXI protein values at the starting material are set to 100%. The main reduction takes place at the Aerosil treatment with subsequent filtration. The downstream process further reduced the FXI protein content to levels of 0.01% of the initial values.

TABLE 14

| Overall reduction of FXI protein (% recovery) from DDCPP starting material to FC | | | | | | | |
|---|---|---|---|---|---|---|---|
| FXI protein recovery | 5 000 IL heparin/I frozen DDCPP | 5 000 IU heparin/ L non-frozen DDCPP | | | | 10 000 IU heparin/ L frozen DDCPP | |
| Cohn pool - DDCPP | 100 | 100 | | | | 100 | |
| Supernatant I | 84 | 91 | | | | 90 | |
| H + HI dissolved | 90 | 88 | | | | 74 | |
| II + III filtrate after Aerosil | 14 | 1.3 | | | | Below quantification limit | |
| CM elution buffer | 35 mM pH 8.5 | 35 mM pH 8.65 | | 35 mM pH 8.5 | | 35 mM pH 8.65 | |
| Ppt G suspension | 1.5 | 1.3 | | 1.3 | | 0.08 | |
| Formulated pH @bulk | pH 4.35 | pH 4.5 | pH 4.65 | pH 4.5 | pH 4.65 | pH 4.5 | pH 4.65 |

TABLE 14-continued

Overall reduction of FXI protein (% recovery) from DDCPP starting material to FC

| FXI protein recovery | 5 000 IL heparin/I frozen DDCPP | 5 000 IU heparin/ L non-frozen DDCPP | | | | 10 000 IU heparin/ L frozen DDCPP | |
|---|---|---|---|---|---|---|---|
| Sterile Bulk | 0.07 | 0.06 | 0.10 | 0.03 | 0.04 | 0.01 | 0.01 |
| Final Container | 0.05 | 0.06 | 0.08 | 0.03 | 0.04 | 0.01 | 0.01 |

Example 8

The level of various protein impurities in the IgG preparations from C1-INH depleted plasma supernatant was then determined. As shown in Table 15, Fibrinogen is below the detection limit (<0.03 μg/mL) and complement C3 level (0.04-0.07 mg/dL) is far below the monitoring limit (<19.4 mg/dL).

TABLE 15

Trace protein content in the final container using 35 mM elution buffer

| Test | Unit | native | Heparin | NaCl |
|---|---|---|---|---|
| C3 complement | [μg/mL] | 0.53 | 0.50 | 0.64 |
| | [μg @ 10% protein] | 0.55 | 0.48 | 0.63 |
| Fibrinogen | [μg/mL] | <0.03 | <0.03 | <0.03 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing an Immunoglobulin G (IgG) enriched fraction from a C1 esterase inhibitor (C1-INH) depleted supernatant fraction comprising IgG, the method comprising:
- (a) contacting the C1-INH depleted supernatant fraction with heparin, thereby forming a heparinized fraction; and
- (b) isolating IgG from the heparinized fraction, thereby forming an IgG enriched fraction.

2. The method of claim 1, wherein the supernatant fraction is a supernatant after C1-inhibitor adsorption.

3. The method of claim 1, wherein the supernatant fraction is a plasma supernatant.

4. The method of claim 3, wherein the plasma supernatant is a C1-INH depleted cryo-poor plasma.

5. The method of claim 1, wherein the supernatant fraction is depleted of one or more of other blood coagulation factors selected from Factor II, VII, IX and X or a mixture thereof.

6. The method of claim 1, wherein the heparin is added in an amount of 1 to 20 units per ml of supernatant fraction.

7. The method of claim 6, wherein the heparin is added in an amount of 5 units per ml of supernatant fraction.

8. The method of claim 6, wherein the heparin is added in an amount of 10 units per ml of supernatant fraction.

9. The method of claim 1, further comprising, prior to step (a), removing C1-INH esterase inhibitor (C1-INH) from a cryo-poor plasma fraction containing C1-INH, thereby forming the C1-INH depleted supernatant fraction.

10. The method of claim 1, wherein the IgG enriched fraction contains at least 50% of the IgG content found in the supernatant fraction.

11. The method of claim 1, wherein the purity of IgG in the IgG enriched fraction is at least 95%.

12. The method of claim 1, wherein said isolating IgG from the heparinized fraction in b) comprises:
- (i) precipitating the heparinized fraction with from 6% to 10% ethanol at a pH of from 7.0 to 7.5 to obtain a Fraction I precipitate and a Fraction I supernatant; and
- (ii) precipitating IgG from the Fraction I supernatant with from 18% to 27% alcohol at a pH of from 6.7 to 7.3 to form a Fraction II+III precipitate.

13. The method of claim 1, wherein said isolating IgG from the heparinized fraction in b) comprises:
- (i) precipitating IgG from the heparinized fraction with from 18% to 27% alcohol at a pH of from 6.7 to 7.3 to form a Fraction I+II+III precipitate.

14. The method of claim 12, further comprising:
- (iii) suspending the Fraction II+III or Fraction I+II+III precipitate in a suspension buffer, thereby forming an IgG suspension;
- (iv) mixing finely divided silicon dioxide ($SiO_2$) with the IgG suspension for at least 30 minutes;
- (v) filtering the IgG suspension, thereby forming a filtrate and a filter cake.

15. The method of claim 14, further comprising:
- (vi) washing the filter cake with at least 1 filter press dead volume of a wash buffer having a pH of from 4.9 to 5.3, thereby forming a wash solution;
- (vii) combining the filtrate with the wash solution, thereby forming a solution, and treating the solution with a detergent;
- (viii) adjusting the pH of the solution of step (vii) to 7.0 and adding ethanol to a final concentration of from 20% to 30%, thereby forming a Precipitate G precipitate;
- (ix) dissolving the Precipitate G precipitate in an aqueous solution comprising a solvent and/or detergent/detergents and maintaining the solution for at least 60 minutes;
- (x) passing the solution through a cation exchange chromatography column and eluting proteins absorbed on the column in an eluate;
- (xi) passing the eluate through an anion exchange chromatography column to generate a generate a flow-through effluent;
- (xii) passing the effluent through a nanofilter to generate a nanofiltrate;
- (xiii) concentrating the nanofiltrate by ultrafiltration to generate a first ultrafiltrate;
- (xiv) diafiltering the first ultrafiltrate against a diafiltration buffer to generate a diafiltrate; and (xv) concentrating the diafiltrate by ultrafiltration to generate a second ultrafiltrate having a protein concentration between 8% (w/v) and 22% (w/v), thereby forming an IgG enriched fraction.

16. The method of claim 14, wherein (iv) comprises adding $SiO_2$ to a final concentration of from 0.02 to 0.10 grams per gram of the Fraction II+III or Fraction I+II+III precipitate.

17. The method of claim 15, wherein (vi) comprises washing the filter cake with at least 2 filter press dead volumes of a wash buffer.

18. The method of claim 15, wherein x) comprises eluting the proteins with at least 35 mM sodium dihydrogen phosphate dihydrate.

19. The method of claim 15, wherein the diafiltration buffer in (xiv) comprises from 200 mM to 300 mM glycine.

20. The method of claim 15, wherein treating the solution with a solvent and/or detergent/detergents in (vii) comprises at least one viral inactivation or removal step.

21. The method of claim 20, wherein the viral inactivation is a solvent/detergent (S/D) viral inactivation step.

22. The method of claim 15, wherein the method further comprises an incubation step at a low pH of from 4.0 to 5.2.

23. The method of claim 15, wherein the method further comprises an incubation step at a low pH of from 4.4 to 4.9.

* * * * *